United States Patent [19]

McCormick

[11] Patent Number: 5,783,579
[45] Date of Patent: Jul. 21, 1998

[54] SPIRO-SUBSTITUTED AZACYCLIC-SUBSTITUTED PIPERAZINO DERIVATIVES AS NEUROKININ ANTAGONISTS

[75] Inventor: Kevin D. McCormick, Edison, N.J.

[73] Assignee: Schering Corporation, Kenilworth, N.J.

[21] Appl. No.: 771,714

[22] Filed: Dec. 20, 1996

[51] Int. Cl.$^6$ .......................... A61K 31/495; A61K 31/54; C07D 401/00; C07D 403/00

[52] U.S. Cl. .......................... 514/255; 514/212; 514/224.5; 540/598; 544/6; 544/231; 544/251; 544/361; 544/364; 544/368; 544/372

[58] Field of Search .......................... 514/224.5, 255, 514/212; 544/6, 251, 361, 364, 368, 372, 231; 540/598

[56] References Cited

U.S. PATENT DOCUMENTS

| | | | |
|---|---|---|---|
| 4,937,246 | 6/1990 | Sugihara et al. | 514/255 |
| 4,997,836 | 3/1991 | Sugihara et al. | 514/253 |
| 5,344,830 | 9/1994 | Mills et al. | 514/235.8 |

FOREIGN PATENT DOCUMENTS

| | | |
|---|---|---|
| WO 94/17045 | 8/1994 | WIPO. |
| WO 94/29309 | 12/1994 | WIPO. |
| WO 96/34864 | 11/1996 | WIPO. |

OTHER PUBLICATIONS

Roderick et al, *J. Med. Chem.*, 9 (1966), pp. 181–185.
Ong et al, *J. Med. Chem.*, 26 (1983), pp. 981–986.
Yamato, et al, *Chem. Pharm. Bull.*, 29 12 (1981), pp. 3494–3498.

Primary Examiner—Mukund J. Shah
Assistant Examiner—Brenda Coleman
Attorney, Agent, or Firm—Anita W. Magatti

[57] ABSTRACT

The invention relates to compounds of the formula

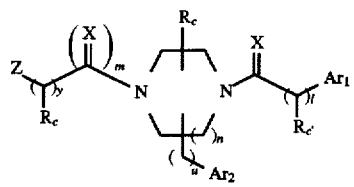

wherein Z, $R_c$, y, m, u, $Ar_2$, n, X, $R_{c'}$, I and $Ar_2$ are as described herein. These compounds are neurokinin antagonists. These compounds are useful in the treatment of chronic airway diseases such as asthma.

6 Claims, No Drawings

SPIRO-SUBSTITUTED AZACYCLIC-SUBSTITUTED PIPERAZINO DERIVATIVES AS NEUROKININ ANTAGONISTS

BACKGROUND OF THE INVENTION

The present invention relates to a genus of compounds useful as antagonists of neurokinin receptors. In particular, these can be neurokinin-1 receptor ($NK_1$) antagonists. Some can also be neurokinin-1 receptor ($NK_1$) antagonists and neurokinin-2 receptor ($NK_2$) antagonists, that is, $NK_1/NK_2$ dual receptor antagonists. Some can also be neurokinin-2 receptor ($NK_2$) antagonists. Some can also be neurokinin-3 receptor ($NK_3$) antagonists.

Neurokinin receptors are found in the nervous system and the circulatory system and peripheral tissues of mammals, and therefore are involved in a variety of biological processes. Neurokinin receptor antagonists are consequently expected to be useful in the treatment or prevention of various mammalian disease states, for example pulmonary disorders like asthma, cough, bronchospasm, chronic obstructive pulmonary diseases, and airway hyperreactivity; skin disorders and itch, for example, atopic dermatitis, and cutaneous wheal and flare; neurogenic inflammation inflammatory diseases such as arthritis, migraine, nociception; CNS diseases such as anxiety, emesis, Parkinson's disease, movement disorders and psychosis; convulsive disorders, renal disorders, urinary incontinence, ocular inflammation, inflammatory pain, and eating disorders such as food intake inhibition; allergic rhinitis, neurodegenerative disorders, psoriasis, Huntington's disease, depression, and various gastrointestinal disorders such as Crohn's disease.

In particular, $NK_1$ receptors have been reported to be involved in microvascular leakage and mucus secretion, and $NK_2$ receptors have been associated with smooth muscle contraction, making $NK_1$ and $NK_2$ receptor antagonists especially useful in the treatment and prevention of asthma.

Moreover, $NK_3$ receptor antagonists are especially useful in the treatment and prevention of asthma, inflammatory diseases and conditions, such as ocular inflammation, allergic rhinitis, cutaneous wheal and flare, psoriasis, atopic dermatitis, CNS diseases such as anxiety and Parkinson's disease.

Spiro-substituted azacyclic $NK_1$ and $NK_2$ receptor antagonists have been disclosed in WO 94/29309, published Dec. 22, 1994, and in WO 94/17045, published Aug. 4, 1994. Piperazino $NK_1$ and $NK_2$ receptor antagonists have been disclosed in WO 96/34864, published Nov. 7, 1996.

SUMMARY OF THE INVENTION

The invention relates to compounds of the formula:

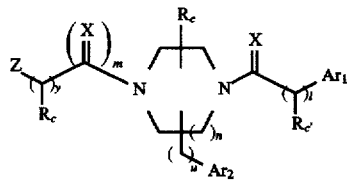

wherein
  each X is independently selected from the group consisting of =O, (H,H), =$NR_d$, and =S;
  n is 0 to 2; u is 0 to 2; 1 is 0 to 2;
  m is 1, and y is 1 to 3; or m is 2, and y is 0;
  each $R_c$ is independently selected from the group consisting of H, $C_1$-$C_6$ alkyl and —$(CH_2)_{n1}$—$R_4$, wherein $n_1$ is 1 to 6, with the proviso that no more than one $R_c$ is other than H in the

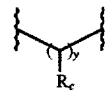

moiety;

$R_d$ is independently selected from the group consisting of H, $C_1$-$C_6$ alkyl, —CN, —$OR_a$, phenyl, substituted phenyl, benzyl, substituted benzyl, or allyl;

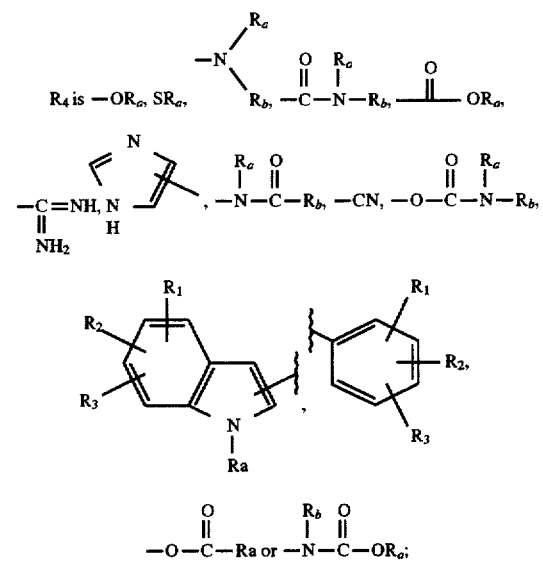

$R_c'$ is H, $C_1$-$C_6$ alkyl or $(CH_2)_nOR_a$, with the proviso that no more than one $R_{c'}$ is other than H;

each $R_a$ and $R_b$ is independently selected from the group consisting of H, $C_1$-$C_6$ alkyl, phenyl, substituted phenyl, benzyl, substituted benzyl and allyl; with the proviso that when $R_4$ is

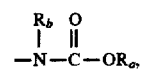

$R_a$ is not H; or when $R_a$ and $R_b$ are attached to the same nitrogen, then $R_a$ and $R_b$, together with the nitrogen to which they are attached, can form a 4 to 7 member ring;

each $R_1$ and $R_2$ is independently selected from the group consisting of H, $C_1$-$C_6$ alkyl, —$CF_3$, —$C_2F_5$, Cl, Br, I, F, —$NO_2$, —$OR_a$, —CN,

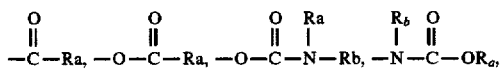

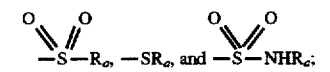

provided $R_a$ is not H in

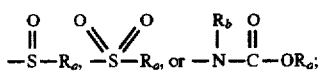

or when $R_1$ and $R_2$ are on adjacent carbons on a ring, they can form

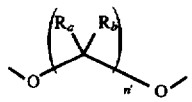

wherein n' is 1 or 2;

each $R_3$ is independently selected from the group consisting of H, $C_1$-$C_6$ alkyl, —$CF_3$, —$C_2F_5$,

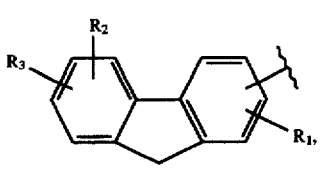

Cl, Br, I, F, —$OR_a$, —$OCF_3$ or phenyl;

$Ar_1$ is heteroaryl or substituted heteroaryl,

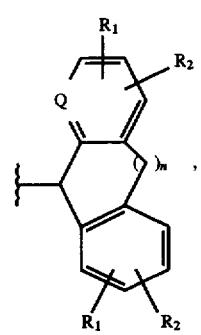

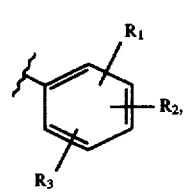

or

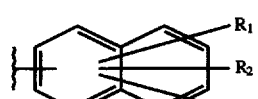

Q is =N— or =CH—;

$Ar_2$ is heteroaryl, substituted heteroaryl,

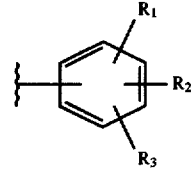

or

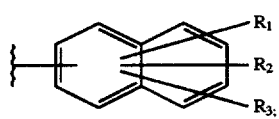

Z is

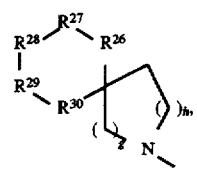

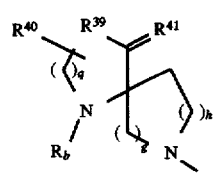

or

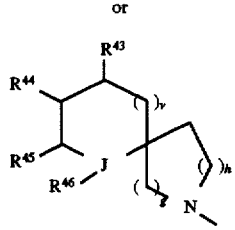

wherein the nitrogen in the unsubstituted ring is optionally quaternized with $C_{1-4}$ alkyl or phenyl-$C_{1-4}$ alkyl or is optionally present as the Noxide ($N^+O^-$);

g and h are each independently 0, 1, 2, 3, 4, or 5, with the proviso that g+h is equal to 1, 2, 3, 4, or 5;

v is 0, 1 or 2;

$R^{26}$ is selected from the group consisting of
(1) a covalent bond
(2) $C_{1-3}$ alkylene, unsubstituted or substituted with a substituent selected from the group consisting of =O, —OH, —$OR^{35}$, halogeno, —$CF_3$, phenyl or mono, di or trisubstituted phenyl, wherein the substituents on the phenyl are independently selected from —OH, —CN, halogeno and —$CF_3$,
(3) $S(O)_k$
(4) ($C_{1-3}$ alkylene)-$S(O)_k$
(5) $S(O)_k$—($C_{1-2}$ alkylene)
(6) $S(O)_k$NH
(7) $S(O)_j$—$NR^{35}$
(8) $S(O)_j$—$NR^{35}$—($C_{1-2}$ alkylene)
(9) CONH
(10) $CONR^{35}$—($C_{1-2}$ alkylene)
(11) $CO_2$ and
(12) $CO_2$—($C_{1-2}$ alkylene)
wherein j is 1 or 2 and k is 0, 1 or 2;

$R^{27}$ is —$NR^{37}$—, —O—, —S—, —S(O)—, or —$SO_2$—, with the proviso that when $R^{26}$ is a covalent bond and $R^{28}$ is $C_{1-3}$ alkyl, $R^{27}$ must be $NR^{37}$;

$R^{37}$ is selected from a group consisting of:
(1) H,
(2) $C_{1-8}$ linear or branched alkyl, unsubstituted, monosubstituted or multiply substituted with —$OR^{35}$, =O, —$NHCOR^{35}$, —$NR^{35}R^{36}$, —CN, -halogeno, —$CF_3$, -phenyl or substituted phenyl, wherein the substituents on phenyl are selected from the group consisting of —OH, —CN, halogeno and —$CF_3$;
(3) S(O)$R^{38}$, wherein $R^{38}$ is $C_{1-6}$ linear or branched alkyl, unsubstituted, mono di or trisubstituted with a substituent selected from the group consisting of =O, —CN, —$OR^{35}$, —$NR^{35}R^{36}$, —$NR^{36}OR^{36}$, -halogeno,—$CF_3$, -phenyl or mono, di or trisubstituted phenyl, wherein the substituents on the phenyl are independently selected from the group consisting of —OH, =O, —CN, —$NR^{35}R^{36}$, —$NR^{35}COR^{36}$, -halogeno, —$CF_3$ and $C_{1-3}$ alkyl;
(4) $SO_2R^{38}$,
(5) $COR^{38}$,
(6) $CO_2R^{38}$;
(7) $CONR^{36}R^{38}$;

$R^{28}$ is selected from the group consisting of
(1) a covalent bond
(2) $C_{1-3}$ alkylene, unsubstituted or substituted with a substituent selected from the group consisting of =O, —$OR^{35}$, halogeno, —$CF_3$, phenyl or mono, di or trisubstituted phenyl, wherein the substituents on the phenyl are independently selected from the group consisting of —$OR^{35}$, halogeno and —$CF_3$;
(3) $S(O)_k$
(4) ($C_{1-3}$ alkylene)-$S(O)_k$
(5) $S(O)_k$—($C_{1-2}$ alkylene)
(6) $NHS(O)_j$
(7) $NH(C_{1-2}$ alkylene)-$S(O)_j$
(8) $S(O)_jNR^{35}$
(9) $S(O)_j$—$NR^{35}$—($C_{1-2}$ alkylene)
(10) NHCO—($C_{1-2}$ alkylene)
(11) $NR^{35}CO$
(12) $NR^{35}$—($C_{1-2}$ alkylene)-CO
(13) O(CO) and
(14) ($C_{1-2}$ alkyl)O(CO);

$R^{29}$-$R^{30}$ considered together are 2 adjoining atoms of the ring

said ring being a phenyl, naphthyl or heteroaryl group, and wherein the phenyl, naphthyl or heteroaryl group is unsubstituted, mono, di or tri substituted, wherein heteroaryl is selected from the group consisting of benzimidazolyl, benzofuranyl, benzoxazolyl, furanyl, imidazolyl, indolyl, isoxazolyl, isothiazolyl, oxadiazolyl, oxazolyl, pyrazinyl, pyrazolyl, pyridyl, pyrimidyl, pyrrolyl, quinolyl, tetrazolyl, thiadiazolyl, thiazolyl, thienyl and triazolyl; and wherein the substituents are independently selected from the group consisting of:
(a) $C_{1-6}$ alkyl, branched or unbranched, unsubstituted or mono or disubstituted by hydroxy
(b) =O
(c) $OR^{35}$
(d) halogeno
(e) $CF_3$
(f) $NO_2$
(g) CN
(h) $NR^{35}R^{36}$
(i) $NR^{35}COR^{36}$
(j) $NR^{35}CO_2R^{36}$
(k) $NR^{35}S(O)_qR^{36}$
(l) $CONR^{35}R^{36}$
(m) $COR^{35}$
(n) $CO_2R^{35}$
(o) $S(O)_qR^{35}$
(p) heteroaryl, or mono or di substituted heteroaryl, wherein heteroaryl is as defined above and the substituents are selected from the group consisting of: $C_{1-6}$ alkyl, branched or unbranched, unsubstituted or mono or disubstituted by OH; =O; $OR^{35}$; $CF_3$; —$NO_2$; CN; $NR^{35}R^{36}$; $NR^{35}COR^{36}$; $NR^{35}CO_2R^{36}$; $NR^{35}S(O)_qR^{36}$; $CONR^{35}R^{36}$; $COR^{35}$; $CO_2R^{35}$; $S(O)_qR^{35}$; and phenyl;

$R^{35}$ and $R^{36}$ are independently selected from:
(a) H,
(b) $C_{1-6}$ alkyl, or mono or disubstituted $C_{1-6}$ alkyl, wherein the substituents independently selected from the group consisting of phenyl, unsubstituted or substituted with —OH, $C_{1-3}$ alkyl, —CN, halogeno, —$CF_3$ or $C_{1-4}$ alkoxy; —OH; =O; —CN; halogeno; or —$CF_3$;
(c) phenyl, pyridinyl or thiophene, or mono, di or trisubstituted phenyl, pyridinyl or thiophene, wherein the substituents are independently selected from the group consisting of —OH, $C_{1-4}$ alkyl, —CN, halogeno and —$CF_3$;
(d) $C_{1-3}$ alkyloxy, or $R^{35}$ and $R^{36}$ are joined together to form a 5-, 6-, or 7-membered monocyclic saturated ring containing 1 or 2 heteroatoms independently selected from nitrogen, oxygen, and sulfur, and in which the ring is unsubstituted or mono or disubstituted, wherein the substituents are independently selected from the group consisting of —OH, =O, —CN, halogeno and —$CF_3$;

q is 1 or 2;

$R^{39}$ is —$NR_b$— or —$CH_2$—;

$R^{40}$ is H, $C_1$-$C_6$ alkyl, =O, phenyl, substituted phenyl, benzyl, substituted benzyl or allyl;

$R^{41}$ is =O or =S;

J is carbon and $R^{43}$, $R^{44}$, $R^{45}$ and $R^{46}$ are independently selected from the group consisting of H, —OH, =O, —$NR^{47}R^{48}$ or —$NR^{47}C(O)$— $NR^{47'}R^{48}$, wherein the nitrogen of —$NR^{47}R^{48}$ is optionally quaternized with $C_{1-4}$ alkyl or phenyl-$C_{1-4}$ alkyl or is optionally present as the N-oxide; or $R^{43}$ and $R^{44}$, or $R^{44}$ and $R^{45}$, together form a carbon-carbon bond; or $R^{43}$ and $R^{44}$ or $R^{44}$ and $R^{45}$, or $R^{45}$ and $R^{46}$, together with the carbons to which they are attached form an aryl or heteroaryl ring, wherein heteroaryl is as defined above, and wherein the aryl or heteroaryl group is unsubstituted, mono, di or tri substituted, wherein the substituents are independently selected from the group consisting of:
(a) $C_{1-6}$ alkyl, branched or unbranched, unsubstituted or mono or disubstituted by hydroxy
(b) =O
(c) $OR^{47}$
(d) halogeno
(e) $CF_3$
(f) $NO_2$
(g) CN (h) NR⁴⁷R⁴⁸
(i) NR⁴⁷COR⁴⁸
(j) NR⁴⁷CO₂R⁴⁸
(k) NR⁴⁷S(O)ⱼR⁴⁸
(l) CONR⁴⁷R⁴⁸
(m) COR⁴⁷
(n) CO₂R⁴⁷
(o) S(O)ₖR⁴⁷
(p) heteroaryl, or mono or di substituted heteroaryl, wherein heteroaryl is as defined above and the substituents are selected from the group consisting of: $C_{1-6}$ alkyl, branched or unbranched, unsubstituted or mono or disubstituted by OH; =O; OR⁴⁷; CF₃; -NO₂; CN; NR⁴⁷R⁴⁸; NR⁴⁷COR⁴⁸; NR⁴⁷CO₂R⁴⁸; NR⁴⁷S(O)ⱼR⁴⁸; CONR⁴⁷R⁴⁸; COR⁴⁷; CO₂R⁴⁷; S(O)ₖR⁴⁷; and phenyl;

or R⁴³, R⁴⁴ and R⁴⁵ are as defined above and J-R⁴⁶ is oxygen or S(O)ᵢ, wherein i is 0, 1, or 2; and R⁴⁷, R⁴⁷' and R⁴⁸ are independently selected from the group consisting of:
(a) H,
(b) $C_{1-6}$ alkyl, or mono or disubstituted $C_{1-6}$ alkyl, wherein the substituents independently selected from the group consisting of phenyl, —OH, =O, —CN, halogeno and —CF₃;
(c) phenyl, naphthyl, or mono, di or trisubstituted phenyl or naphthyl, wherein the substituents are independently selected from the group consisting of —OH, $C_{1-3}$ alkyl, —CN, halogeno and —CF₃; and
(d) $C_{1-3}$ alkyloxy; or R⁴⁷ and R⁴⁸ are joined together to form a 5-, 6-, or 7-membered monocyclic saturated ring containing 1 or 2 heteroatoms independently selected from nitrogen, oxygen, and sulfur, and in which the ring is unsubstituted or mono or disubstituted, wherein the substituents are independently selected from the group consisting of —OH, =O, —CN, halogeno and —CF₃;

or any enantiomer or diastereomer thereof, or a pharmaceutically acceptable salt thereof.

All of the variables in the above formulas such as Z, R₁, R₂, and R₃, have the same meaning throughout the specification unless otherwise specified.

Preferred compounds of the invention are compounds of formula I wherein each X is =O or (H,H) and at least one X is =O.

Also preferred are compounds of formula I wherein each X is =O.

Also preferred are compounds of formula I wherein l is 0, m is 1, n is 1, u is 0 and y is 1–3.

Also preferred are compounds of formula I wherein Ar₁ is

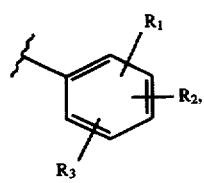

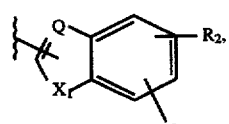

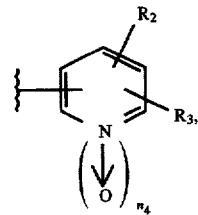

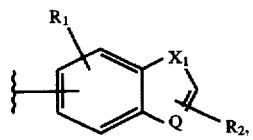

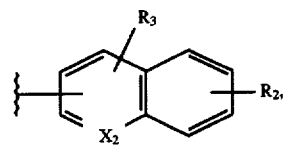

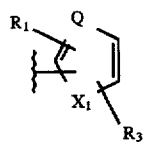

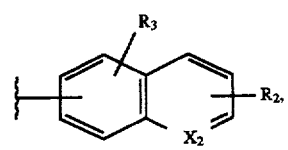

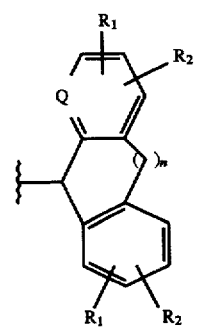

or

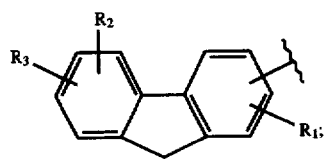

wherein Q is =N— or =CH—;

each X₁ is independently —O—, —S— or —NRₐ—;

each X₂ is independently =CH— or —N=; and n₄ is 0 or 1; and

AR$_2$ is
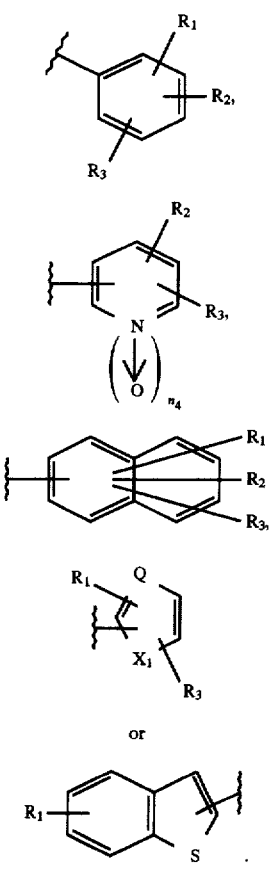
Also preferred are compounds of formula I wherein each X is =O; l is 0; m is 1; y is 1–3; n is 1; u is 0; Ar$_1$ is
—continued
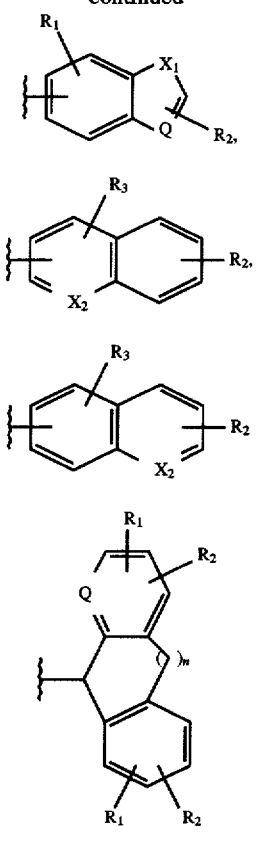
and Ar$_2$ is
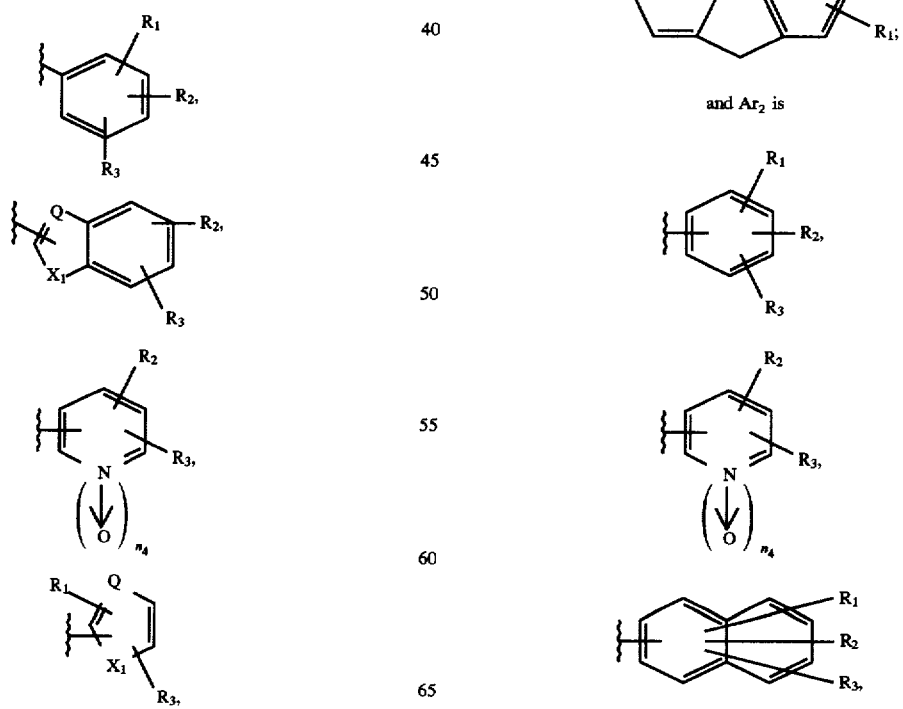

-continued

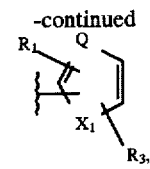

or

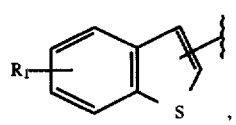

wherein $n_4$ is 0 or 1.

Preferred definitions of Z having the spirocyclic structure

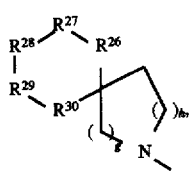

are exemplified by the following structures, optionally substituted at the positions indicated by numbers 1–8 with —OH, =O, —CN, —$NR^{35}R^{36}$, —$NHCOR^{35}R^{36}$, halogeno, —$CF_3$, phenyl, mono, di or trisubstituted phenyl, wherein the phenyl substituents are independently selected from the group of substituents defined immediately above and $C_{1-3}$ alkyl:

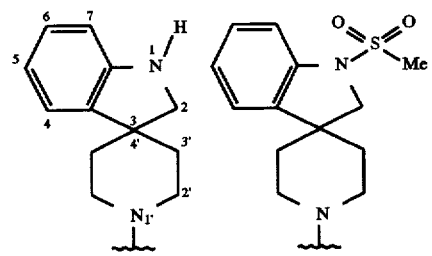

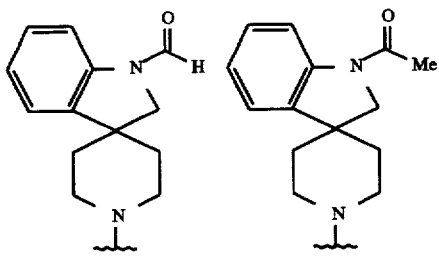

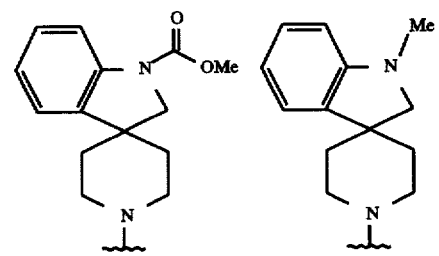

-continued

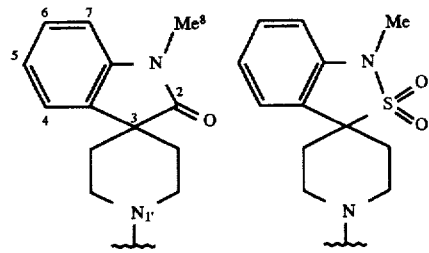

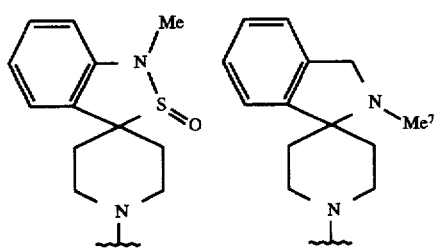

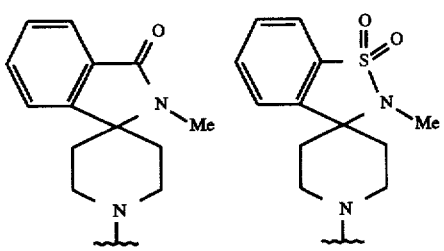

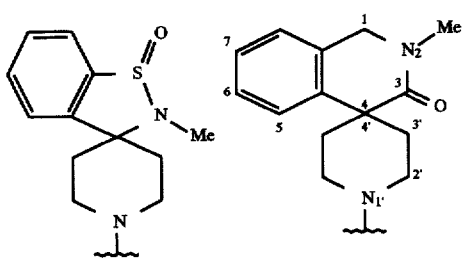

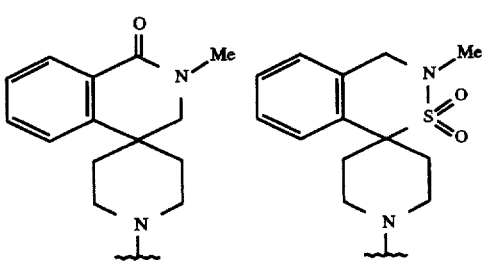

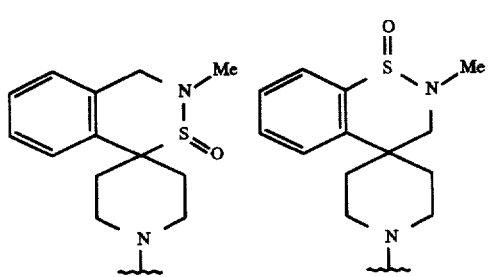

-continued
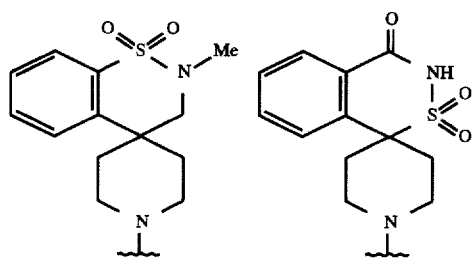
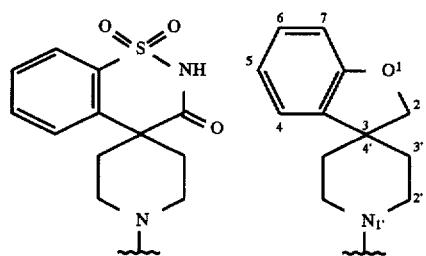
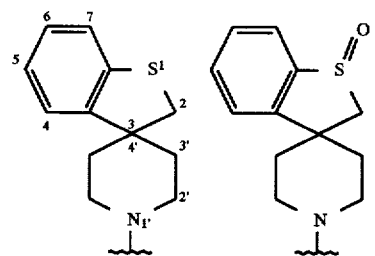
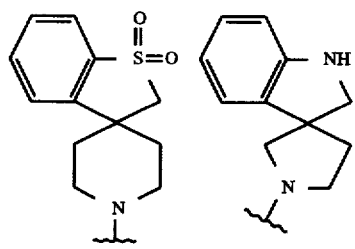
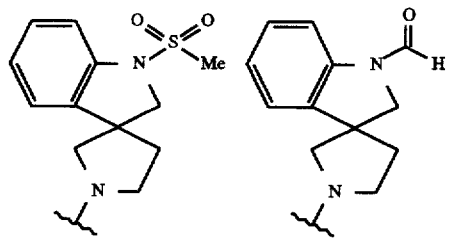
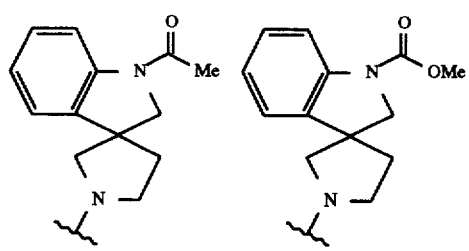
-continued
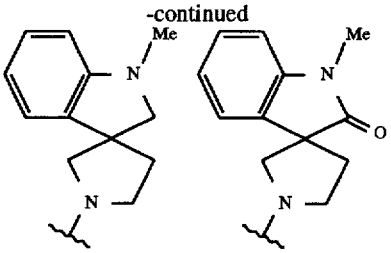
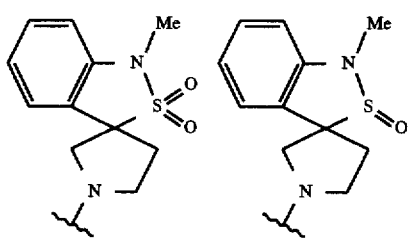
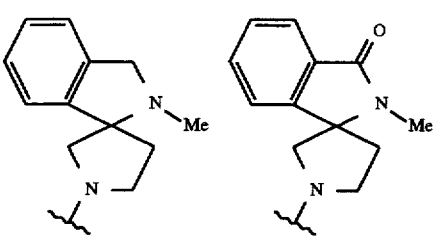
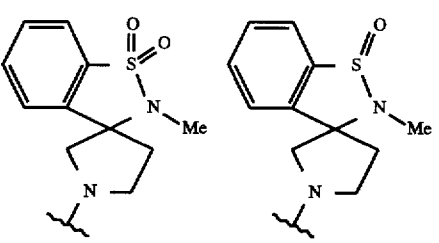
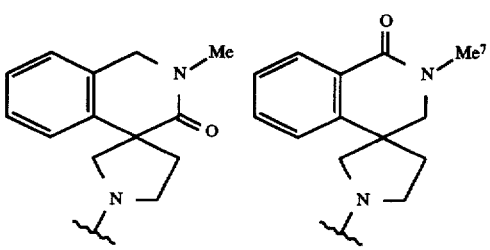
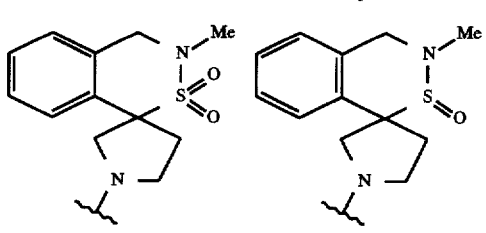
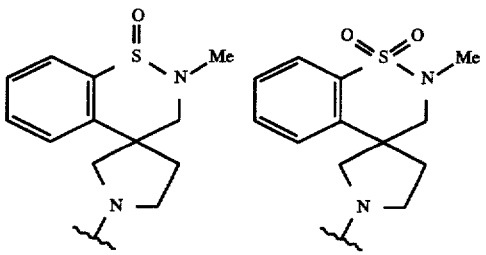

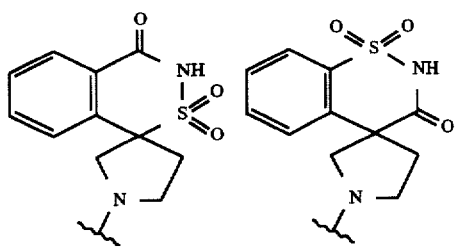
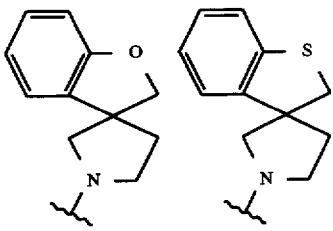
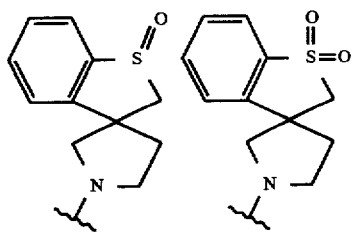
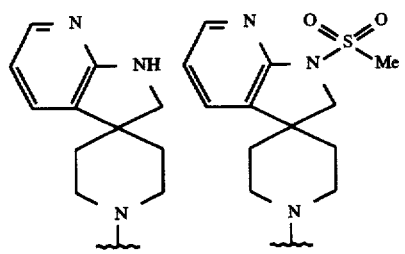
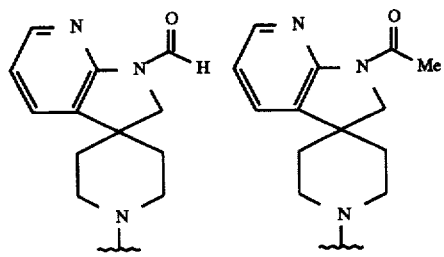
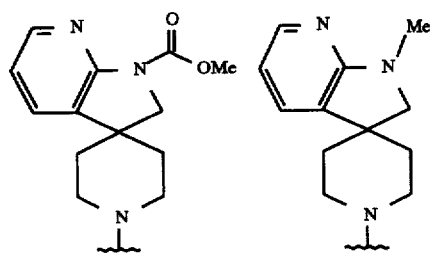
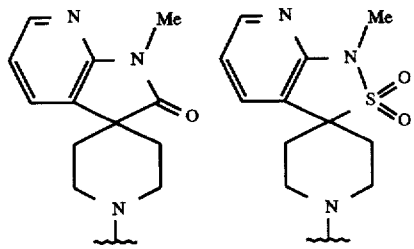
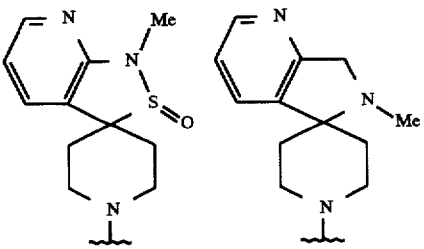
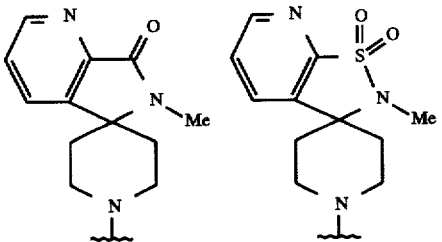
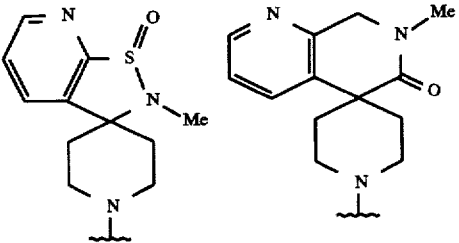
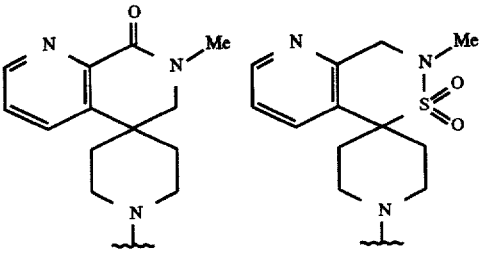
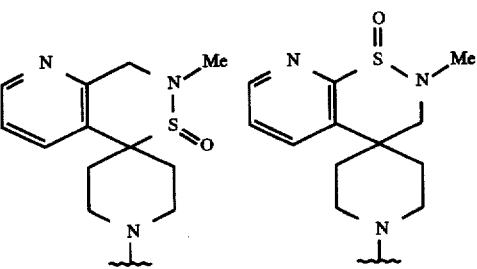

-continued

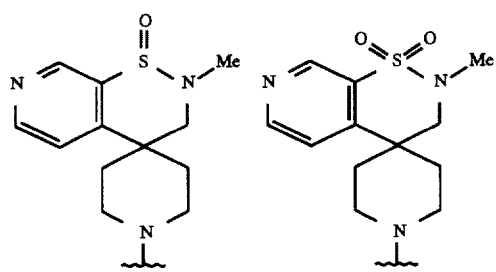
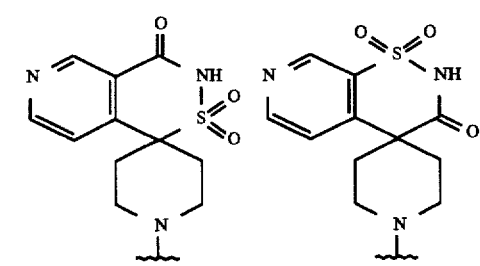
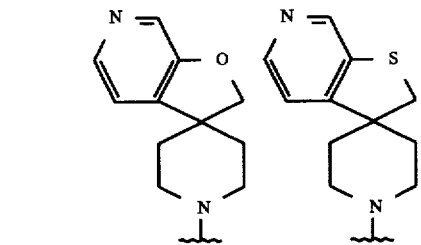
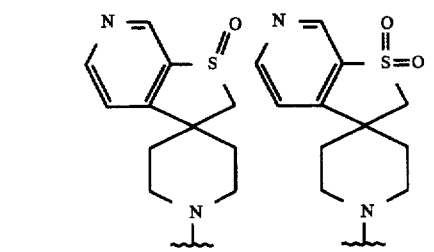
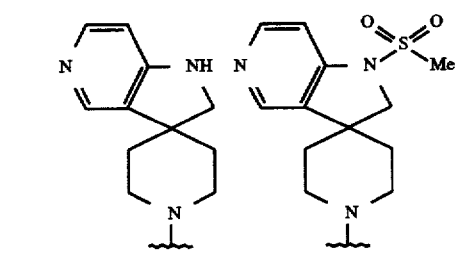
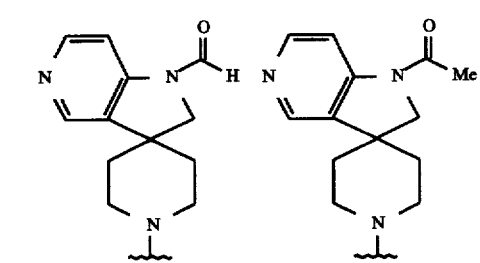
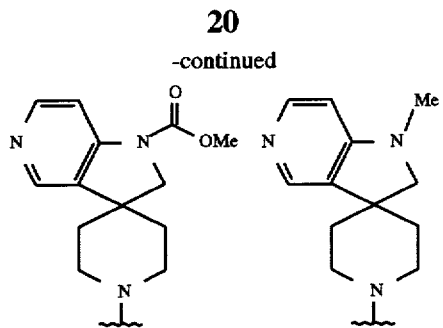
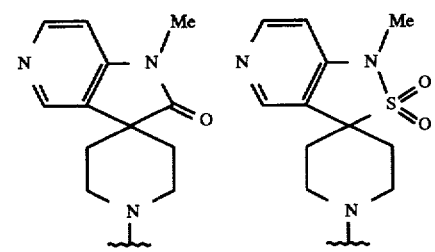
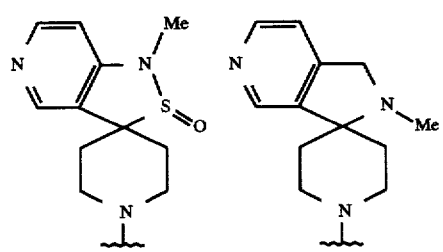
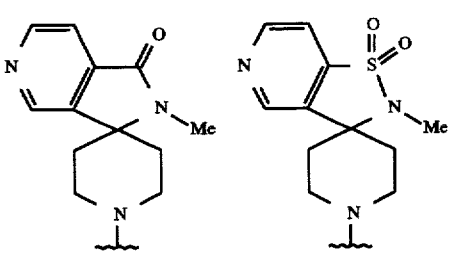
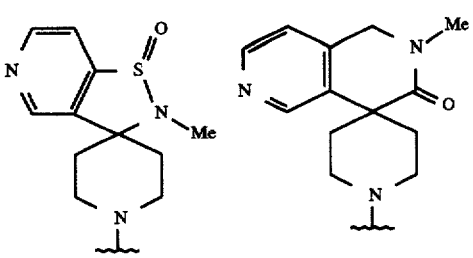
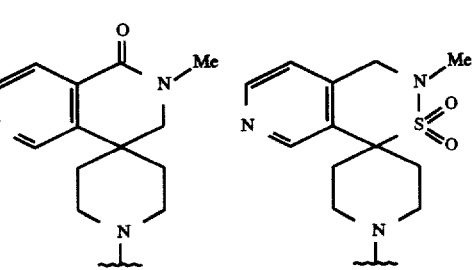

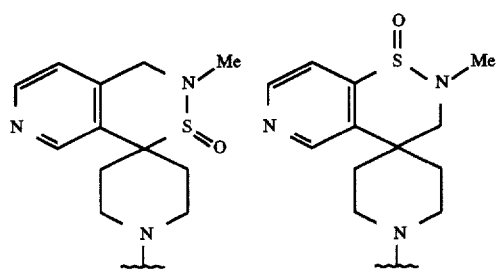
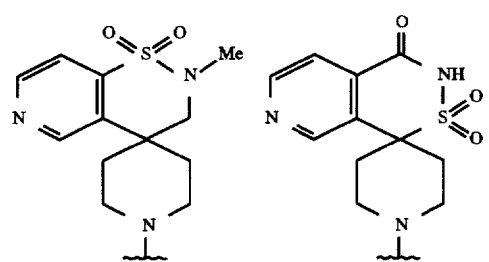
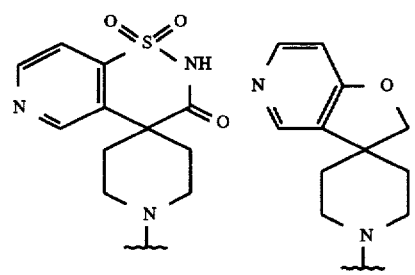
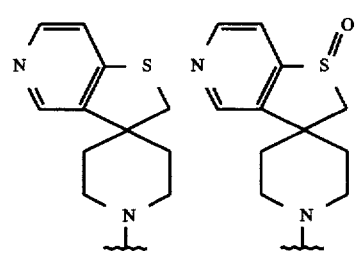
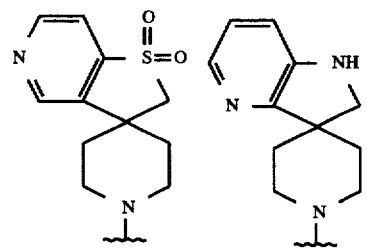
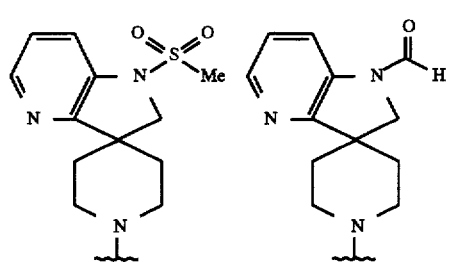
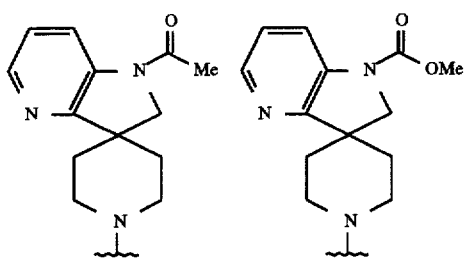
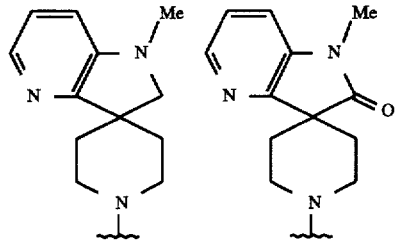
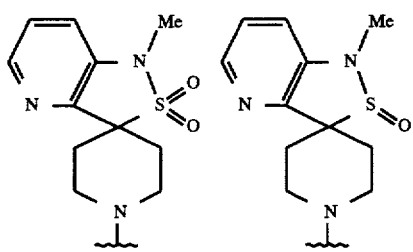
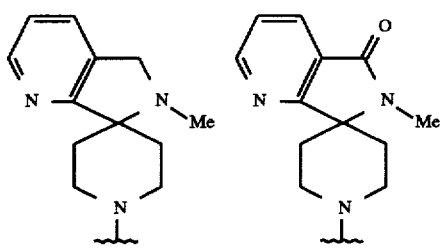
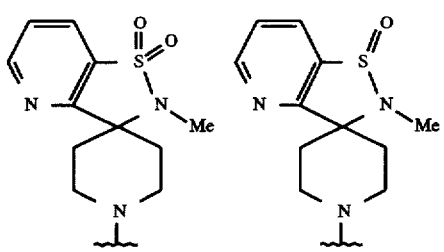
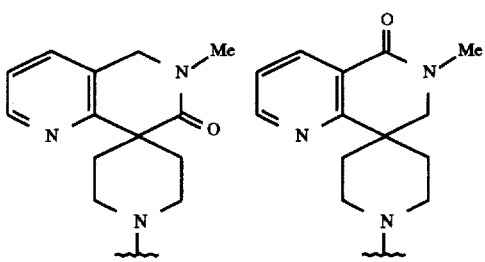

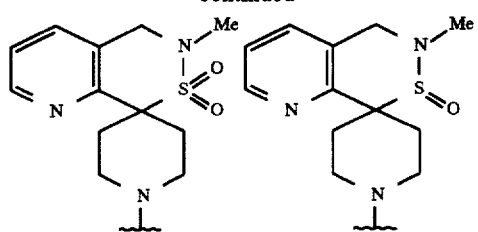
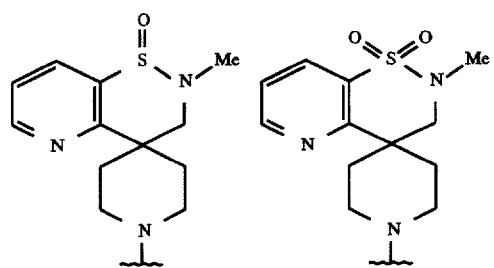
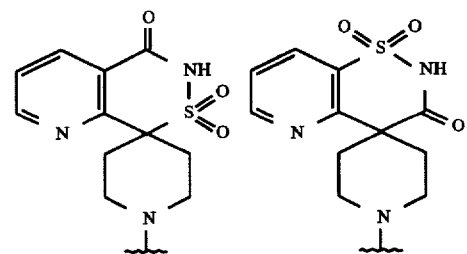
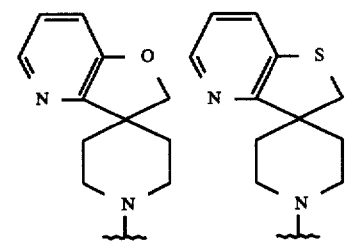
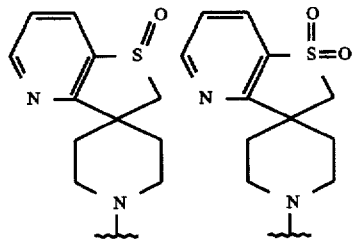
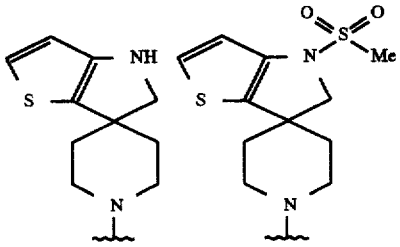
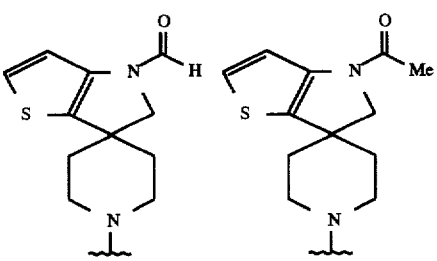
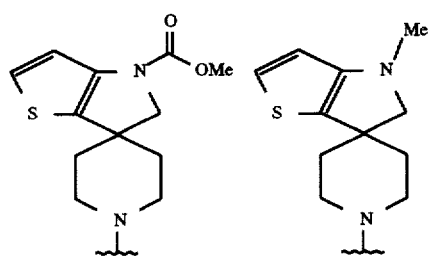
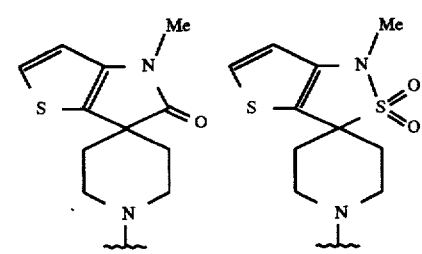
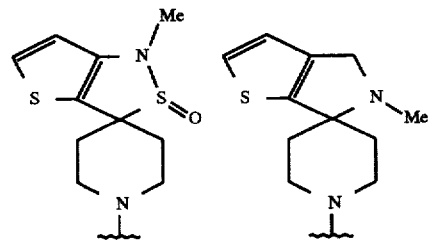
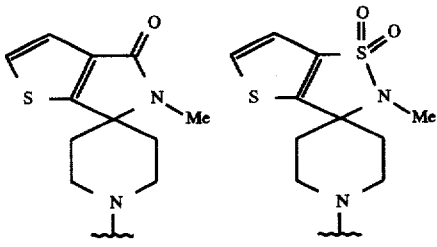
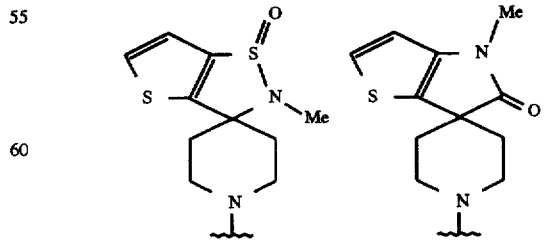

-continued
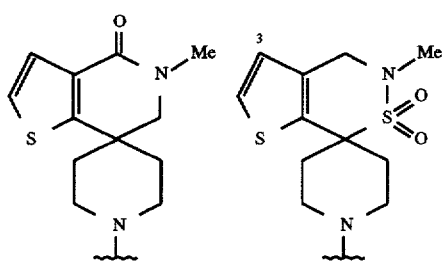
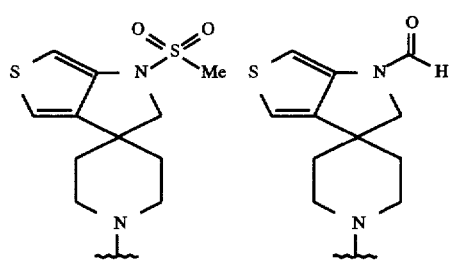
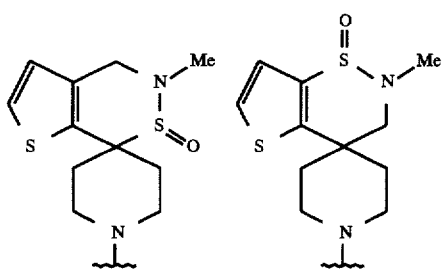
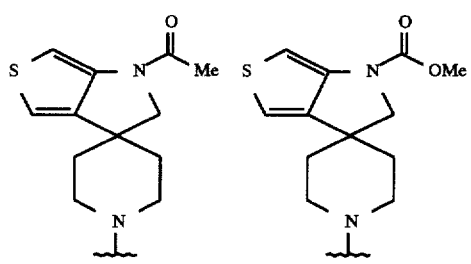
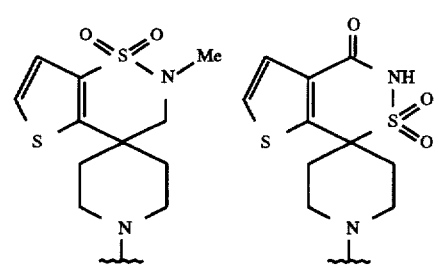
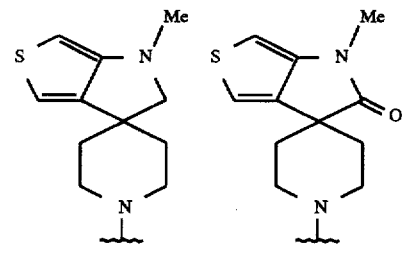
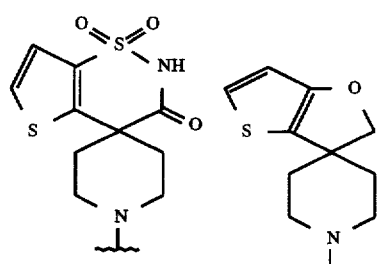
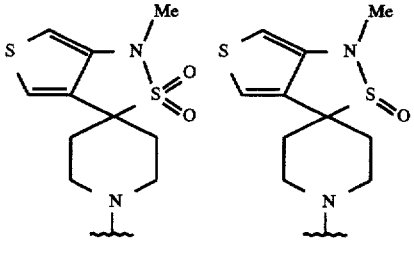
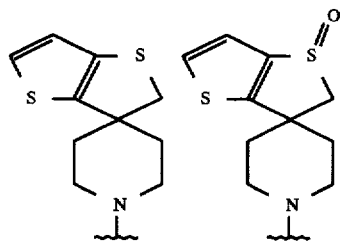
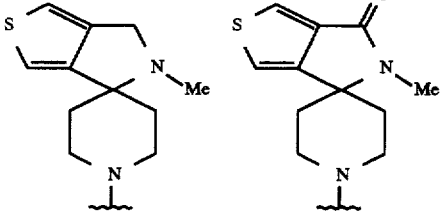
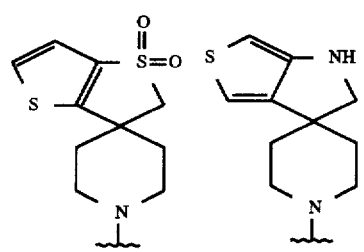
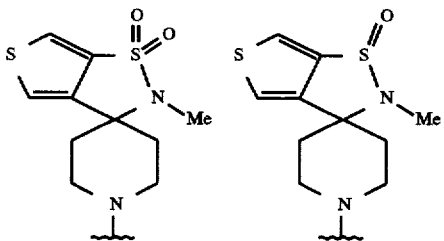

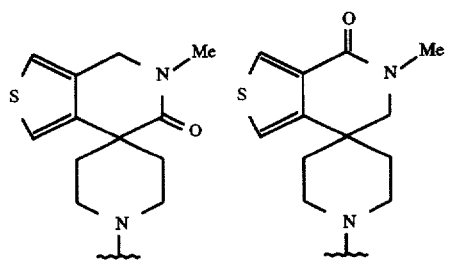
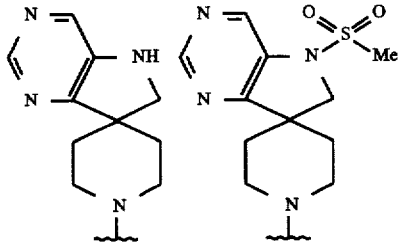
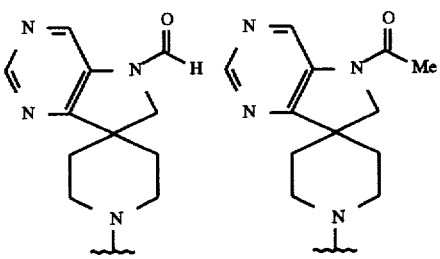
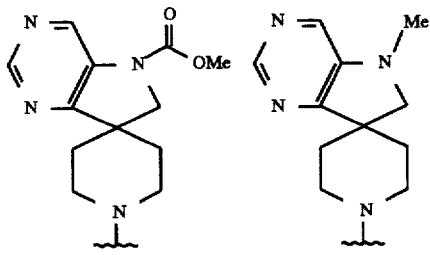
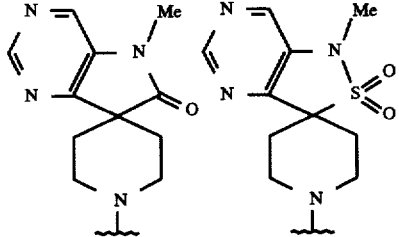
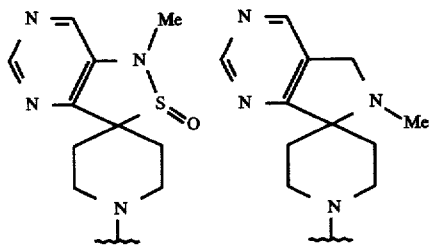
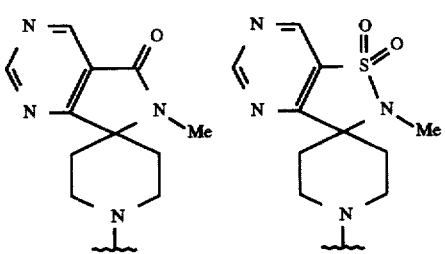

-continued
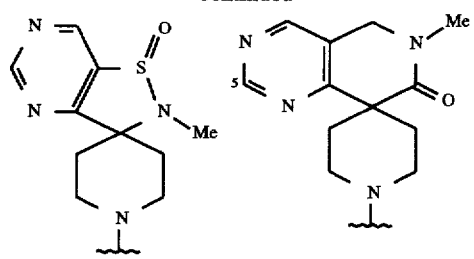
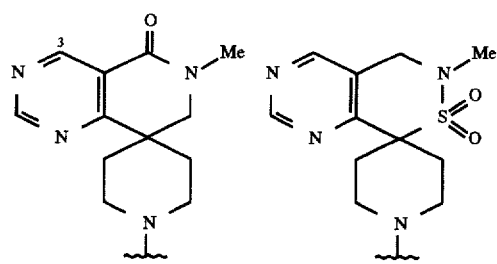
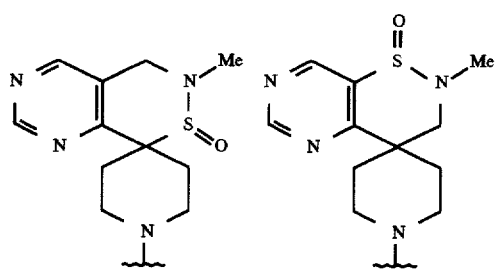
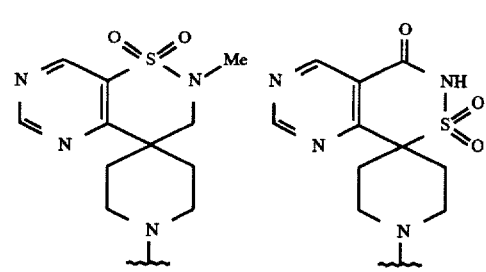
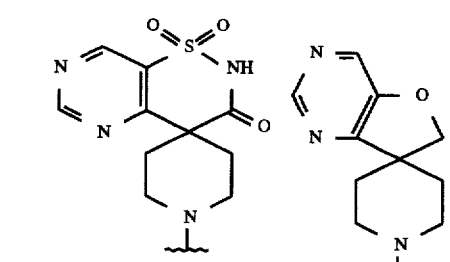
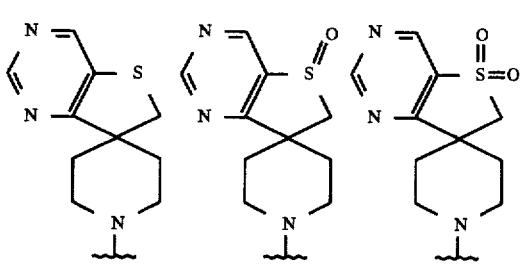
Preferred definitions of Z having the spirocyclic structure
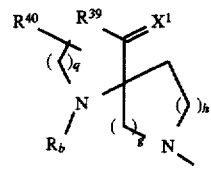
are exemplified by the following structures:
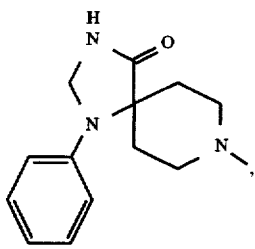
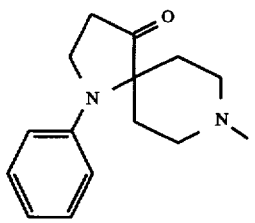
and
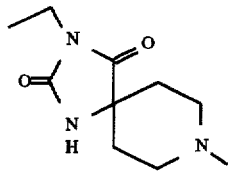
Preferred definitions of Z having the spirocyclic structure
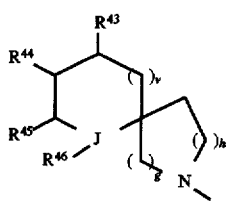
are exemplified by the following structures:
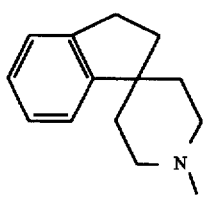

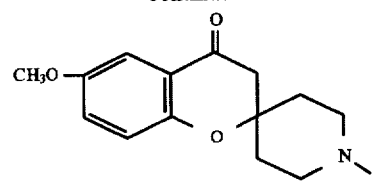
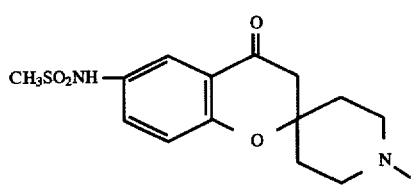
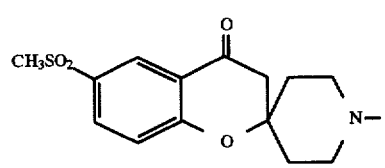
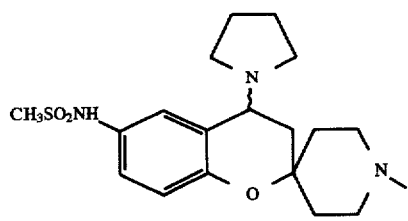
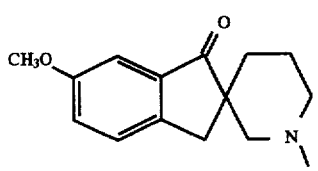
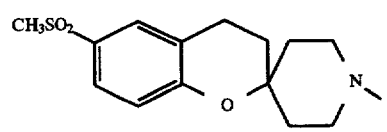
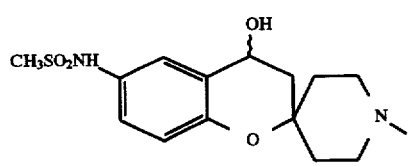
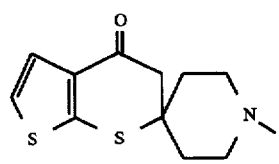
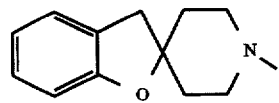
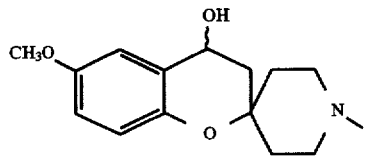
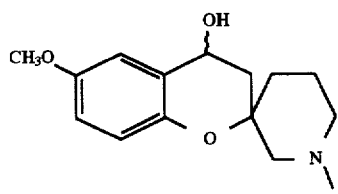
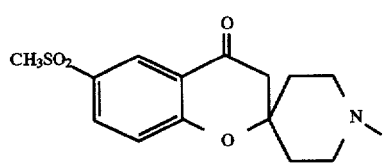
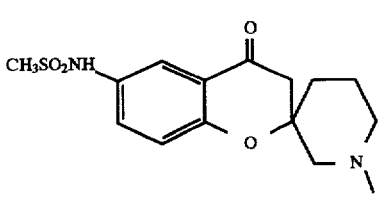
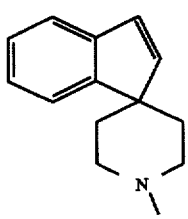
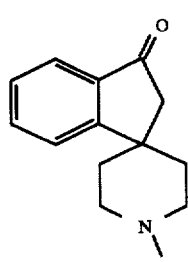
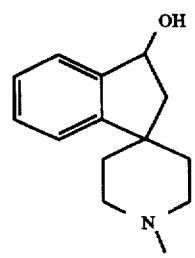

-continued

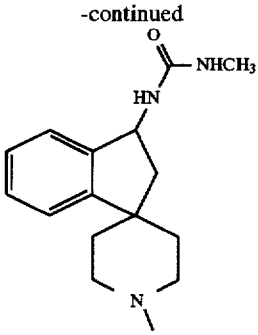

Especially preferred definitions of Z are:

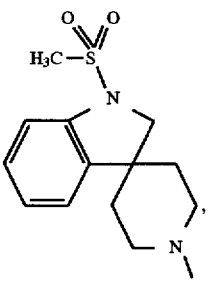

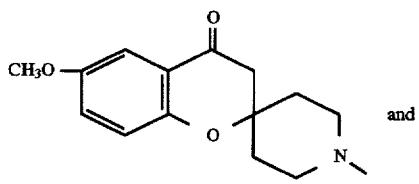
and

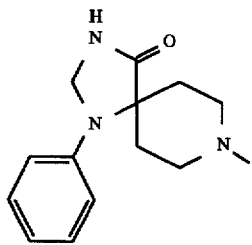

or any stereoisomer thereof, including any enantiomer, diastereomer, R or S form thereof, or a pharmaceutically acceptable salt thereof.

The invention also relates to a pharmaceutical composition comprising a therapeutically effective amount of a compound of formula I in combination with a pharmaceutically acceptable carrier.

The invention also relates to a method for inducing neurokinin antagonism which comprises administering a neurokinin antagonistic effective amount of a compound of formula I to a mammal in need thereof.

The invention also relates to a method for treating chronic airway diseases such as asthma and allergies; inflammatory diseases such as inflammatory bowel disease, psoriasis, fibrositos, osteoarthritis, and rheumatoid arthritis; migraine; central nervous system disorders such as emesis, depression, psychosis, dementia, and Alzheimer's disease; Down's syndrome; neuropathy; multiple sclerosis; ophthalmic disorders; conjunctivitis; auto immune disorders; graft rejection; systemic lupus erythematosus; GI disorders such as Crohn's disease and ulcerative colitis; disorders of bladder function; circulatory disorders such as angina; Raynaud's disease; coughing and pain. In particular, the invention also relates to a method of treating asthma which comprises administering to a mammal in need of such treatment an anti-asthma effective amount of a compound of formula I for such purpose.

DETAILED DESCRIPTION OF THE INVENTION

As used herein the term alkyl means a straight or branched, saturated hydrocarbon chain having from 1 to 6 carbon atoms. The number of carbon atoms may be designated. For example, "$C_1$–$C_6$ alkyl" represents a straight or branched, saturated hydrocarbon having from 1 to 6 carbon atoms.

The term $C_3$–$C_6$ cycloalkyl means a cycloalkyl having from 3 to 6 carbon atoms, that is cyclopropyl, cyclobutyl, cyclopentyl and cyclohexyl.

The term alkenyl means a straight or branched, saturated alkenyl having from 2 to 6 carbon atoms. The number of carbon atoms may be designated. For example, "$C_2$–$C_6$ alkenyl" represents a straight or branched alkenyl having from 1 to 6 carbon atoms.

The term alkynyl means a straight or branched alkynyl having from 2 to 6 carbon atoms. The number of carbon atoms may be designated. For example, "$C_2$–$C_6$ alkynyl" represents a straight or branched chain alkynyl having from 2 to 6 carbon atoms.

As used herein, a heavy dark line (—◼) denotes a chemical bond coming above the plane of the page. A dashed line (⋯⋯ɪ) denotes a chemical bond coming below the plane of the page.

As used herein,

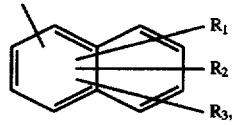

for example, means that $R_1$, $R_2$, and $R_3$ can be in either of the rings of the above naphthyl moiety.

Asymmetric centers exist in compounds of formula I of the invention. Accordingly, compounds of formula I include stereoisomers, i.e., enantiomers, diastereomers, endo and exo forms.

All such isomeric forms and mixtures thereof are within the scope of the present invention. Unless otherwise indicated, the methods of preparation disclosed herein may result in product distributions which include all possible structural isomers, although it is understood that physiological response may vary according to stereochemical structure. The isomers may be separated by conventional means such as fractional crystallization, preparative plate or column chromatography on silica, alumina, or reversed phase supports or HPLC (high performance liquid chromatography).

Enantiomers may be separated, where appropriate, by derivatization or salt formation with an optically pure reagent, followed by separation by one of the aforementioned methods. Alternatively, enantiomers may be separated by chromatography on a chiral support.

The compounds of formula I can exist in unsolvated as well as solvated forms, including hydrated forms, e.g. the hemihydrate. In general, the solvated forms, with pharmaceutically acceptable solvents such as water, ethanol, and the like are equivalent to the unsolvated forms for the purposes of the invention.

Those compounds of formula I which contain a basic group such as —$CH_2NH_2$, form pharmaceutically acceptable salts. The preferred pharmaceutically acceptable salts are nontoxic acid addition salts formed by adding to a suitable compound of the invention about a stoichiometric amount of a mineral acid, such as HCl, HBr, $H_2SO_4$ or $H_3PO_4$ or of an organic acid such as acetic, propionic, valeric, oleic, palmitic, stearic, lauric, benzoic, lactic, para-toluenesulfonic, methanesulfonic, citric, maleic, fumaric, succinic and the like, respectively.

GENERAL METHODS OF PREPARATION

The compounds of this invention may be prepared by one of the following general methods. As used herein RT means room temperature. Unless otherwise indicated, variables in the structural formulas below are as defined above. Starting materials and reagents used in the methods and examples below, are known or may be prepared according to known methods.

As used herein the term "substituted phenyl" means

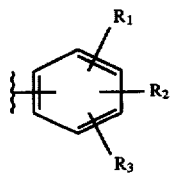

wherein $R_1$, $R_2$, and $R_3$ are as described herein.

"Substituted" means substituted by $R_1$, $R_2$, and/or $R_3$ as described herein.

"Aryl" means phenyl, naphthyl, indenyl, tetrahydronaphthyl, indanyl, anthracenyl or fluorenyl.

"Halogeno" refers to fluoro, chloro, bromo or iodo atoms.

"Heterocycloalkyl" refers to 4- to 6-membered rings comprising 1 to 3 heteroatoms independently selected from the group consisting of —O—, —S— and —$N(R^6)$—, with the remaining ring members being carbon. Examples of heterocycloalkyl rings are tetrahydrofuranyl, pyrrolidinyl, piperidinyl, morpholinyl, thiomorpholinyl and piperazinyl.

"Heteroaryl" refers to 5- to 10-membered single or benzofused aromatic rings comprising 1 to 3 heteroatoms independently selected from the group consisting of —O—, —S— and —N=. Examples of single-ring heteroaryl groups are pyridyl, isoxazolyl, oxadiazolyl, furanyl, pyrrolyl, thienyl, imidazolyl, pyrazolyl, tetrazolyl, thiazolyl, thiadiazolyl, pyrazinyl, pyrimidinyl, pyridazinyl and triazolyl. Examples of benzofused heteroaryl groups are quinolinyl, thianaphthenyl (i.e., benzothienyl) and benzofurazanyl. N-oxides of nitrogen-containing heteroaryl groups are also included. All positional isomers are contemplated, e.g., 1-pyridyl, 2-pyridyl, 3-pyridyl and 4-pyridyl.

Where $R^2$ and $R^3$ substituents form a ring and additional heteroatoms are present, the rings do not include adjacent oxygen and/or sulfur atoms or three adjacent heteroatoms. Typical rings so formed are morpholinyl, piperazinyl and piperidinyl.

As used herein, the term "BOC" means t-butoxycarbonyl.

As used herein, the term "Ph" means phenyl.

As used herein, the term "parallel synthesis" means the preparation of individual chemical compounds as one of a batch of, for instance, 20, 30, or even 100 identical reactions on usually a single substrate but using a different reagent in each vessel. Such reagents are always of the same general class- in this case, either carboxylic acids or organic amines in any set of parallel reactions. The conditions used for each reaction are identical to those described in the examples, except that a simplified work-up is employed, generally a simple wash either with acid or base if appropriate, then water. The presence of the product is detected by thin layer chromatography (TLC) using known products as representative standards. Further characterization by combination HPLC/MS is generally performed. No further purification is performed on these materials before they are submitted to biological assays.

As used herein, each $R_c$ and $R_{c'}$ is independently selected from the group consisting of H, $C_1$–$C_6$ alkyl, $C_2$–$C_6$ alkenyl, $C_2$–$C_6$ alkynyl, unsubstituted or substituted phenyl, and unsubstituted or substituted benzyl, The starting materials in the methods below are either known or can be prepared in accordance with known methods. In particular, the following compounds are either known or can be prepared in accordance with known methods: the diamine A, the compounds of formulas A, VI, VIII, X, XI, XIV, XVIII, XIX, XXa, A', XXV, and Z—H, as well as esters of formula XI, and compounds of formula

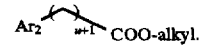

Method 1. If the group $Ar_2$ is an aromatic group with no I or Br substituents, then the following method may be used to prepare the useful intermediates (IV):

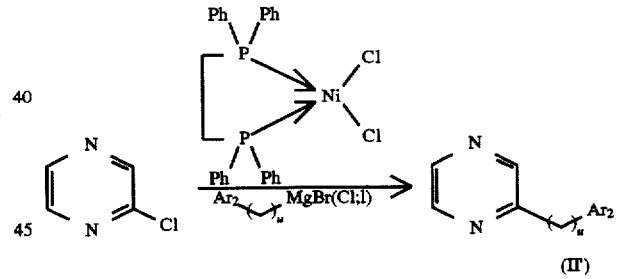

Transition metal catalyzed coupling of 2-chloropyrazine with an aromatic Grignard reagent in a dry, ether solvent, such as THF, yields the aryl-substituted pyrazine of formula II'. The catalyst shown, [1,2-bis-(diphenylphosphino)ethane]nickel" chloride, is a preferred reagent for this transformation. Where $Ar_2$ has no halo substituents, reduction of a compound of formula II' by catalytic hydrogenation, using, for instance, palladium acetate, preferably in acetic acid solvent, results in preferential reduction of the pyrazine ring, leaving the aromatic ring unreduced, that is, it results in a compound of formula II. Similarly, 10% Pd on charcoal (Pd—C) can be used in an alcohol solvent, preferably methanol, with or without the addition of a small quantity (1 to 5 equivalents) of acetic acid. Reaction times of about 1 to 24 hours generally suffice for this reaction, which is preferentially run at room temperature or slightly above (up to about 50° C.) and using from 1 to about 6 atmospheres pressure of hydrogen.

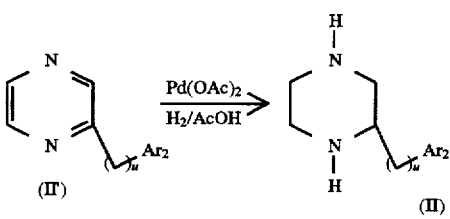

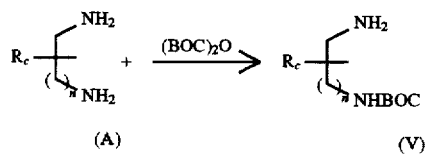

The intermediate of formula II may also be prepared from a compound of formula II', even if the group Ar₂ contains halogen atoms, by reduction using a strong hydride ion donor, preferably lithium aluminum hydride (LAH) or diisobutyl aluminum hydride (DIBAL-H) in an ether solvent, such as ether, THF or dimethoxyethane (DME).

Selective alkylation of a compound of formula II is possible using low temperature conditions. Thus, reacting a compound of formula II with a substituted aryl-alkyl halide of formula III where l is 0 to 2, results in the formation of the 4-substituted derivative of formula IV. Suitable conditions include use of a halogenated solvent, such as CH₂Cl₂, at low temperature. Suitable temperatures are from -78° C. initially, allowing the reaction mixture to warm gradually to RT if the reaction is not completed after several hours. The reaction is catalyzed by the addition of an equivalent amount of an organic base, such as triethylamine and diisopropylethylamine (Hünig's base).

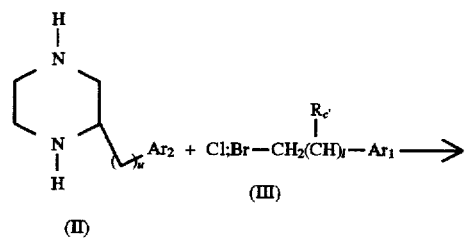

Method 2. If the group Ar₂ contains one or more halogen atoms on an aromatic ring and the other groups are as in Method 1, then an alternate route to a compound of formula IV is preferred. In addition, this method can be used to prepare compounds in which l is from 0 to 2. Mono-protection of the diamine of formula (A), preferably with BOC anhydride, or other agents known to introduce the t-butyloxycarbonyl protecting group, in an alcohol solvent, such as methanol, preferably at about -10° C., produces a compound of formula V.

These compounds are used to perform a reductive amination reaction with the aldehyde of formula VI to produce an amine of formula VII. (In structures (A), (V), (VII), and (IX) herein, R_c can be bound to any position between the two nitrogens. In cyclic structures like (IVA) below, R_c can be bound to any available cyclic position that is occupied by carbon, and that is between the two nitrogens.)

Suitable conditions for this type of reaction include the use of an alcohol solvent, preferably methanol, or 2,2,2-trifluoroethanol, made slightly acidic with a weak organic acid, such as acetic acid, and a reducing agent known to favor reductive amination reactions, preferably sodium cyanoborohydride, NaBH₃CN.

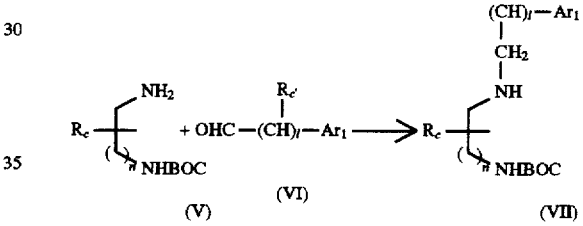

Reaction of a compound of formula VII with an (α-haloketone of formula VIII, in which Ar₂ preferably represents a halogenated aromatic ring, but may be any of the claimed aromatic rings, in the presence of an organic base, such as diisopropylethylamine, also known as H ünig's Base, in an ether solvent, such as THF, results in the formation of the intermediates of formula IX.

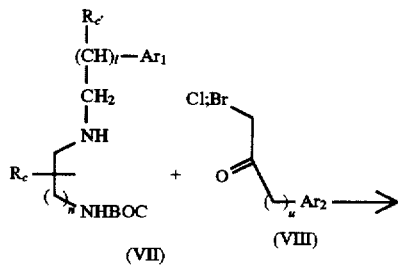

-continued

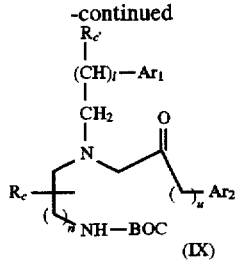

(IX)

Removal of the BOC protecting group using a suitable acidic catalyst, such as trifluoroacetic acid, followed by an intramolecular reductive amination, under conditions such as those described above for the preparation of a compound of formula VII, leads to the formation of compounds of formula IVA.

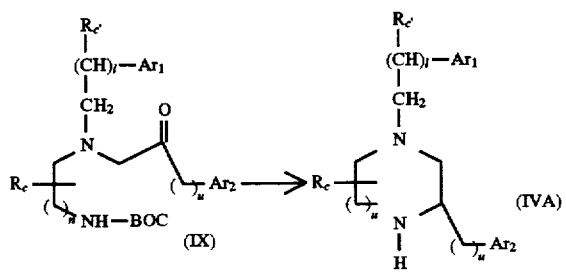

Method 3. An alternate route to compounds of the invention in which l is 0 to 2 is as follows. Standard coupling of an N-protected amino acid of formula X, wherein $Ar_2$ is as described above, with an amino acid ester derivative

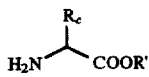

(R' is $C_2$–$C_4$ alkyl, preferably, the ethyl ester of formula XI, .Et in the formulas herein means ethyl), produces a dipeptide of formula XII. A suitable protecting group is BOC, although many others may also be used. Other esters of the amino acid may also be used. Standard coupling techniques may be applied, an example being the use of N-hydroxybenztriazole (HOBT) and a water-soluble carbodiimide, such as 1-(3-dimethylaminopropyl)-3-ethylcarbodiimide (DEC), in a non-hydroxylic solvent such as $CH_2Cl_2$, DMF or a mixture of the two foregoing solvents. The reaction is run, preferably, at or below RT, and takes from 1 to 40 hours for completion, depending upon the substrates.

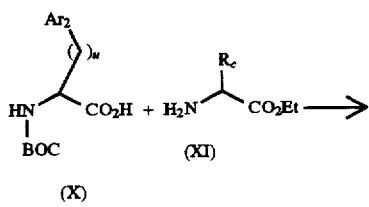

-continued

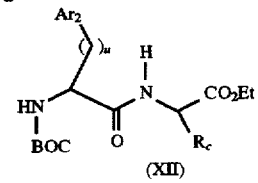

(XII)

Removal of the protecting group under standard conditions, followed by treatment of the product with a base results in cyclization to the diketopiperazine of formula XIII. Suitable conditions for removal of the exemplified BOC group are well known in the art and include catalysis by trifluoroacetic acid (TFA). A suitable base for cyclization is the alkali metal salt of an alcohol in the alcohol itself used as solvent. For example, a solution of sodium ethoxide in ethanol may be used. The temperature is preferably around RT but may be slightly above or below, in the range 0° C. to about 40° C. The reaction is generally complete within a few hours. Suitable reaction times are from 1 to 24 hours.

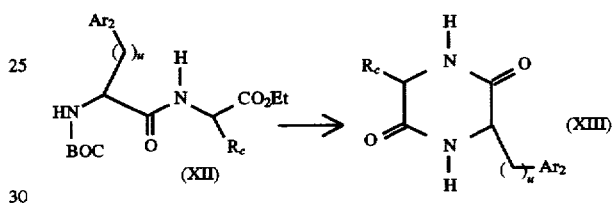

Reduction of the diketopiperazine of formula XIII to a compound of formula II may be accomplished preferentially with a strong hydride reducing agent, such as LAH or a solution of sodium bis(2-methoxyethoxy)aluminum hydride in toluene (also known as Red-Al®), or the $BH_3 \cdot S(CH_3)_2$ complex. Suitable solvents for this reaction are DME and other higher boiling ethers since the reaction is run at elevated temperatures, from about 50° C. to about 110° C., preferably about 90° C.

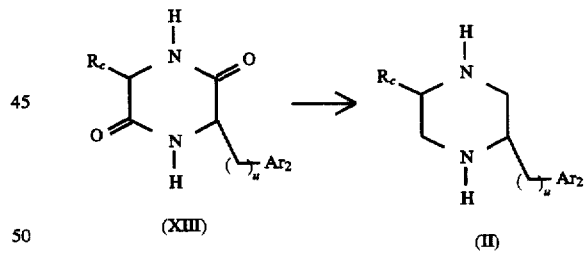

Alternatively, a compound of formula of II may be prepared by the scheme shown below (J. Med. Chem., 9, 191 (1966)). As used herein L is any readily available ester residue such as $C_1$–$C_7$ alkyl, more preferably methyl or ethyl.

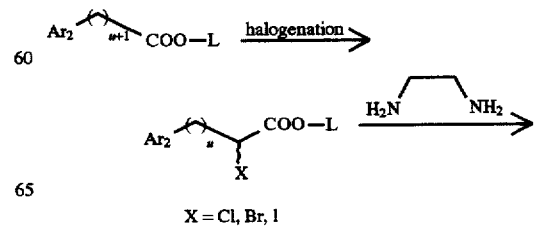

X = Cl, Br, I

-continued

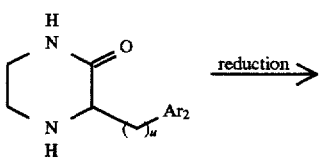

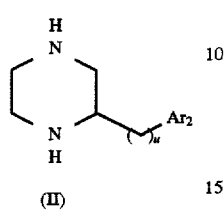

(II)

A compound of formula II may be converted to a compound of formula IV by the processes described in Method 1 above or Method 6 below.

Method 4. The intermediates of formula IV or IVA, formed via any of the previous methods, may be further processed as follows. A compound of formula IVA will be used in the Schemes. Reaction of a compound of formula IVA with an activated halo-acid, generally the acid halide of formula XIV, in which Hal represents Cl, Br, or I, yields the acylated derivative of formula XV that is, m is 1 for formula I. An organic base is used to take up the hydrogen halide formed in the reaction, suitable bases being triethylamine (TEA) and Hünig's Base. Suitable reaction media include halogenated solvents, such as methylene chloride and chloroform. The reaction is preferably run at low temperature, at least initially. Suitable temperatures are in the region of –50° C. down to –80° C. Later in the reaction it may be desirable to allow the mixture to warm up to about RT to ensure completion of the reaction.

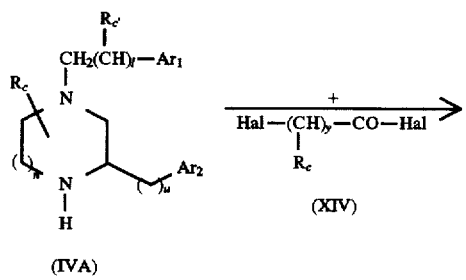

(IVA)

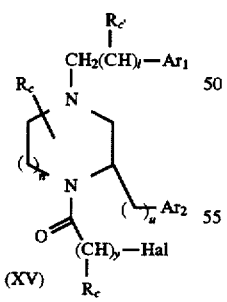

(XV)

Reaction of the halogenated amides of formula XV with an amine of formula Z—H results in formation of the products of formula XVI, which are compounds of the invention in which X is O and m is 1. Compounds of formula XVI have been modified to show the fact that these products could have been prepared from compounds of formula IVA as well as from IV. Suitable solvents for this reaction are halogenated hydrocarbons, such as methylene chloride, and an organic base is present to absorb the H-Hal formed. Appropriate bases include Hünig's Base. The reaction is performed at or around RT, a suitable temperature being generally in the range of from 0° C. to 40° C. Reaction is complete within 1 to 48 hours.

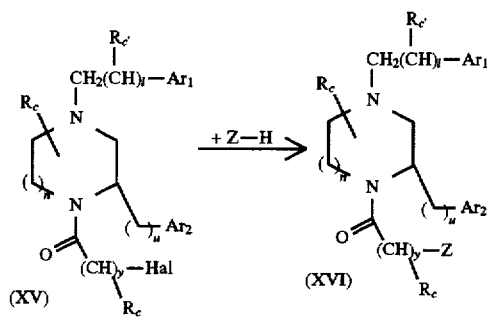

Method 5. Compounds of formula XVI where y≠0 may be converted to other compounds of the invention of formula XVII by reduction under controlled conditions.

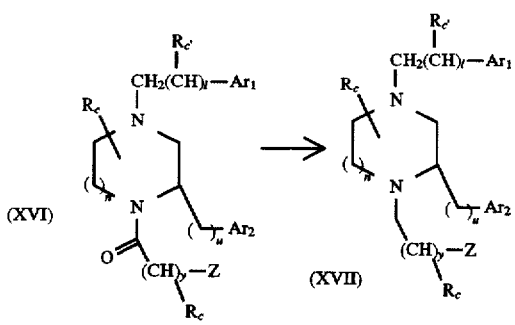

Suitable reducing agents to effect this transformation include the borane-dimethyl sulfide complex, as well as other less selective reagents, such as LAH, (assuming that no other group reactive to LAH is present), Red-Al®, and diborane in ether. Effective temperatures for the borane-dimethylsulfide complex to reduce compounds of formula XVI, range from RT to the reflux temperature of the solution of the reagent in THF (about 80° C.).

Method 6. Intermediates of the formula XVIII may be selectively acylated by coupling with an acid of the formula XIX. Standard coupling techniques may be applied, for example the use of HOBT, a water-soluble carbodiimide, such as DEC, and an organic base, such as $Et_3N$, in a non-hydroxylic solvent, such as $CH_2Cl_2$, at a temperature of about –20° C. initially. The mixture may be allowed to warm to RT to complete the reaction. The product of reaction is the amide of formula XX.

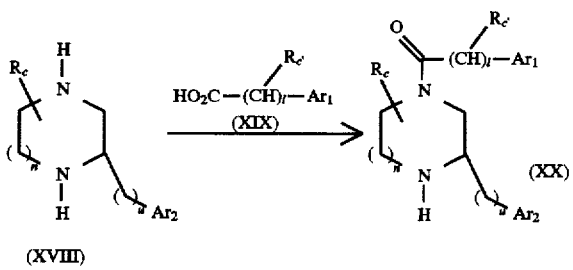

(XVIII)

Compounds of the formula XX, may be further acylated using an acid halide of formula XIV. The reaction is run, preferably at about 0° C., over a period of 1 to 12 hours, in a halogenated solvent, such as methylene chloride or similar solvent. An organic tertiary amine is used to absorb the H-Hal produced in the reaction. Suitable amines include triethylamine and Hünig's Base. As used herein Hal means Cl, Br, or I.

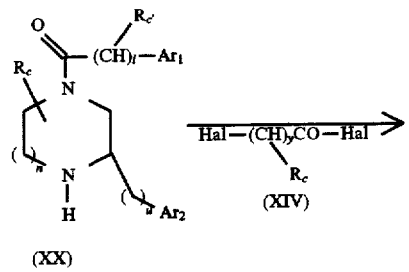

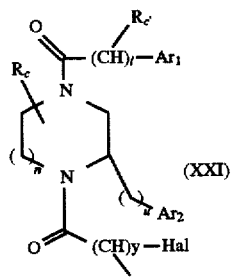

The compounds of formula XXI, that is, m is 1 in formula I, y=1–3, l=0–2 may be used for further reaction without isolation. Additional organic base, for instance, Hünig's Base, is added to the mixture followed by Z—H, at or around −78° C. The reaction is completed by allowing the mixture to warm to RT overnight yielding the compounds of formula XXII after work-up and purification by standard methods.

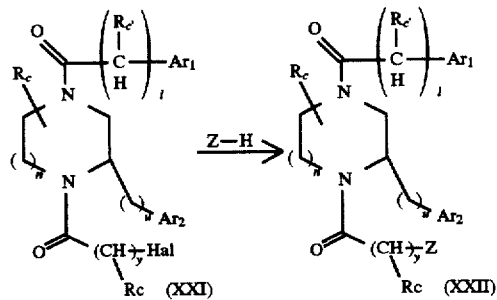

The compounds of formula XXII, in which y=1–3 may be converted to other products of formula XXIII by reduction under controlled conditions.

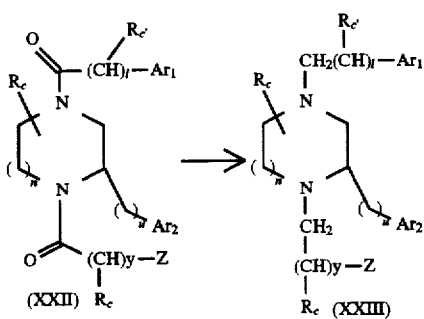

Suitable reducing agents to effect this transformation include the borane-methyl sulfide complex, as well as other less selective reagents, such as LAH, Red-Al®, and diborane in ether or other unreactive solvents, such as THF. Using the borane-methyl sulfide complex in THF, at the reflux temperature of the solution, which is about 80° C., the reaction is complete in about 2 hours to 48 hours depending on the precise substrate.

Method 7. The acylated derivatives of formula XX from Method 6 may be reduced to the saturated alkyl chain derivatives of formula IVA.

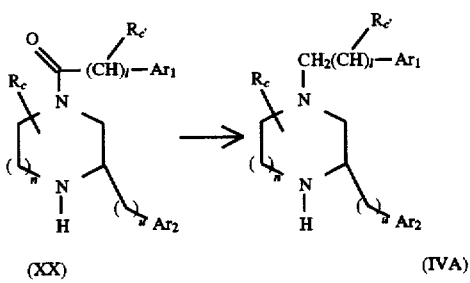

The process to conduct this conversion is the same as described in Method 6 for conversion of a compound of formula XXII to a compound of formula XXIII. The reagent of preference is the borane-methyl sulfide complex.

A compound of formula IVA can be converted to a target compound of formula XVI as described previously.

An alternate route to compounds of structure (XXII) also starts with compound (XVIII). Initial reaction with an amine protecting group reagent, preferably BOC anhydride, produces the N-t-butyloxycarbonyl derivative of the formula XXVIII.

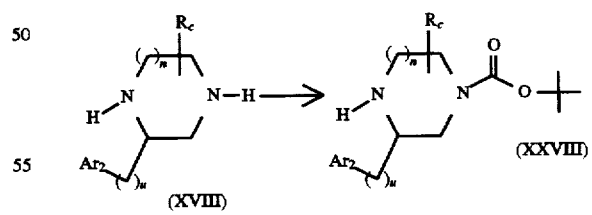

As before, reaction occurs preferentially at the nitrogen atom further away from the $Ar_2$ group. Reaction of this intermediate with a reagent of structure (XIV) as described above, leads to the halo-derivative (XXIX). Reaction of (XXIX) with Z—H, again as described above, produces the intermediate (XXX) which may be de-protected to produce (XXXI). Suitable reagents include trifluoroacetic acid and HCl.

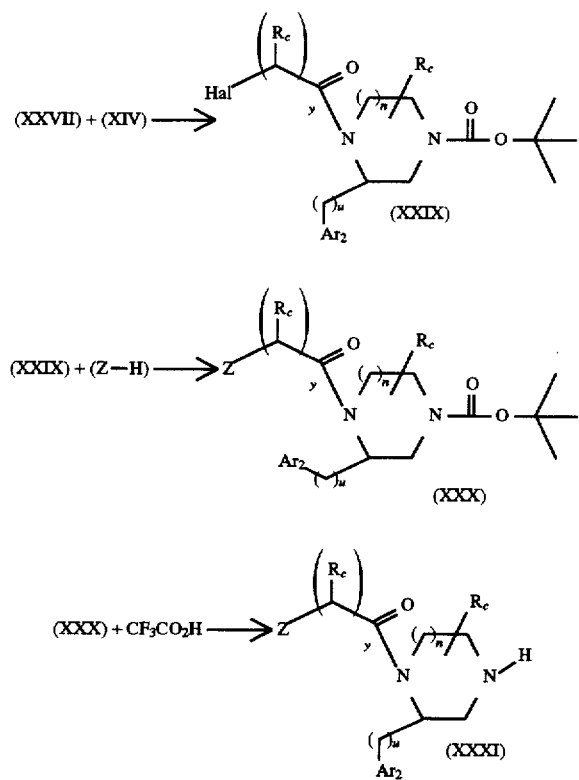

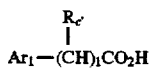

Reaction of (XXXI) with a carboxylic acid (XIX) under coupling conditions as described above, leads to the products of formula (XXII). Method 7a. Synthesis of the compounds of the invention wherein the pendant aromatic group $Ar_2$, or the pendant aromatic group $Ar_2$ and its sidechain, are located in the alternate ring position to the compounds of formula XXII (i.e. compounds of formula C below), may be prepared using compounds of formula XXVIII from method 7 as starting materials. Coupling of compounds of formula XXVIII with any of the acids $$Ar_1-(CH)_lCO_2H$$
with $R_{c'}$ above under standard coupling conditions, for instance using HOBT, $Et_3N$ and DEC in $CH_2Cl_2$, produces the intermediate (A). Removal of the t-BOC or other protecting group under standard conditions releases the free amine (B). Acylation of (B) and further reaction with Z—H proceeds as described in Method 6 for the conversion of (XX) via (XXI) to (XXII) to produce compound (C) of the invention.

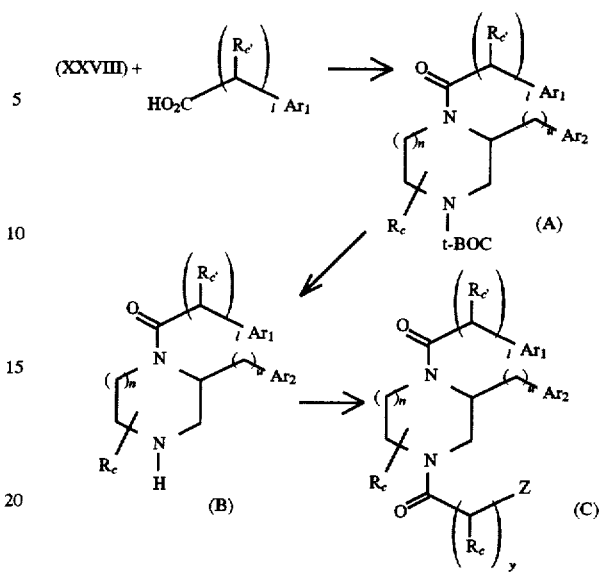

The Z—H starting materials are commercially available or are prepared using methods known in the art.

Using procedures similar to those described in the above or using procedures known to those skilled in the art, one can produce all of the compounds of formula I of the invention. For example, one can obtain compounds of the invention of formula I wherein the $R_c$ moiety is on various carbons of the piperazine ring.

The in vitro and in vivo activity of the compounds of formula I can be determined by various procedures known in the art, such as a test for their ability to inhibit the activity of the $NK_1$ agonist Substance P, an isolated hamster trachea $NK_2$ assay, a test of the effect of $NK_1$ antagonists on Substance P-induced airway microvascular leakage, measurement of $NK_2$ activity in vivo in guinea pigs, measurement of bronchoconstriction due to NKA, and neurokinin receptor binding assay(s). Typical procedures are published in previously cited WO96/34864.

For all of the compounds of the invention, the $NK_1$ binding is in a range of about 0-100% inhibition at 1 μM concentration. For all of the compounds of the invention, the $NK_2$ binding is in a range of about 0-100% inhibition at 1 μM concentration. It should be understood that while the NK binding for certain compounds of the invention is as low as 0% at 1 μM concentration, that at higher concentrations these compounds are expected to have NK binding inhibition activity.

The $K_i$ of a compound is that concentration at which the compound caused 50% inhibition of either $NK_1$ or $NK_2$. For those compounds of the invention having higher than 50% inhibition of $NK_1$, $K_i$'s for $NK_1$ are determined.

For those compounds of the invention having higher than 50% inhibition of $NK_2$, $K_i$'s for $NK_2$ are determined.

Compounds of formula I exhibit $NK_1$ and $NK_2$ antagonist activity to varying degrees, i.e., certain compounds have strong $NK_1$ antagonist activity, but weaker $NK_2$ antagonist activity. Others are strong $NK_2$ antagonists, but weaker $NK_1$ antagonists. Certain compounds have both strong $NK_1$ and $NK_2$ antagonist activities. Some compounds can also be $NK_3$ antagonists.

Many compounds of formula I have an asymmetric center and therefore exist as a pair of enantiomers. In such cases, one enantiomer can have different biological activity than the other. For example, one enantiomer can have strong $NK_1$ activity and weak $NK_2$ activity while the other enantiomer has weak $NK_1$ activity and strong $NK_2$ activity.

Certain compounds of formula I have been found to be antagonists of both $NK_1$ and $NK_2$ receptors, and are therefore useful in treating conditions caused or aggravated by the activity of $NK_1$ and $NK_2$ receptors.

The present invention also relates to a pharmaceutical composition comprising a compound of formula I and a pharmaceutically acceptable carrier. Compounds of this invention can be administered in conventional oral dosage forms such as capsules, tablets, powders, cachets, suspensions or solutions, or in injectable dosage forms such as solutions, suspensions, or powders for reconstitution. The pharmaceutical compositions can be prepared with conventional excipients and additives, using well known formulation techniques. Pharmaceutically acceptable excipients and additives include nontoxic and chemically compatible fillers, binders, disintegrants, buffers, preservatives, antioxidants, lubricants, flavorings, thickeners, coloring agents, emulsifiers and the like.

The daily dose of a compound of formula I for treating asthma, cough, bronchospasm, inflammatory disease, migraine, nociception and gastrointestinal disorders is about 0.1 mg to about 20 mg/kg of body weight per day, preferably about 0.5 to about 15 mg/kg, more preferably 0.5 to about 5 mg/kg. For an average body weight of 70 kg, the dosage range is therefore from about 1 to about 1500 mg of drug per day, preferably about 50 to about 100 mg, given in a single dose or 2–4 divided doses. The exact dose, however is determined by the attending clinician, and is dependent on the potency of the compound administered, the age, weight, condition and response of the patient.

The invention disclosed herein is exemplified by the following examples, which should not be construed to limit the scope of the disclosure. Alternative mechanistic pathways and analogous structures within the scope of the invention will be apparent to those skilled in the art.

PREPARATIVE EXAMPLE 1

2-(3,4-dichlorophenyl)piperazine

A. Synthesis of racemic compound 2-(3,4-Dichlorophenyl)piperazine was synthesized according to the method published in *J. Med.Chem.* 9, 191, 1966.

A. General method for the synthesis of 2-aryl-piperazine derivatives.

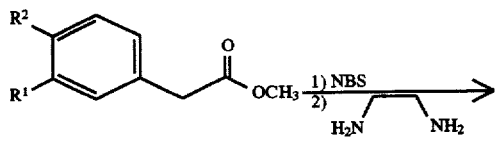

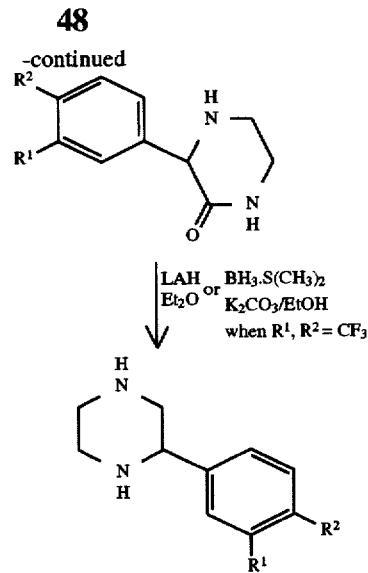

$R^1$ = Cl, H or other substituents i.e. $OCH_3$, $CF_3$, Br, I, F, etc.
$R^2$ = Cl, H or other substituents i.e. $OCH_3$, $CF_3$, Br, I, F, etc.

B. Resolution of 2-(3,4-dichlorophenyl)piperazine

Step 1: A solution of 2-(3,4-dichlorophenyl)piperazine (36.05 g, 0.156 mol) in $CH_3OH$ (200 mL) was treated with a solution containing two equivalents of N-acetyl-L-leucine (54.02 g, 0.312 mol) and heated until all of the material was dissolved. EtOAc (2.2 L) was added to this solution and allowed to stand at ambient temperature overnight. The solvent phase was decanted from the precipitated salt and concentrated in vacuo. This procedure was repeated using 37.88 g of 2-(3,4-dichlorophenyl)piperazine (0.164 mol) and 56.68 g of N-acetyl-L-leucine (0.327 mol).

Step 2: The concentrated salts from both solvent phases in step 1 were combined and heated in methanol (550 mL) until all of the material dissolved. EtOAc (2.75 L) was added to this solution and allowed to stand at ambient temperature overnight. The solvent phase was decanted from the precipitated salt and concentrated in vacuo to give ~95 g of piperazine salt (72% ee of enantiomer A).

Step 3: The salt from the solvent phase in step 2 was dissolved in a solution of $H_2O$ (800 mL) and aq. ammonia (400 mL) and extracted with $CH_2Cl_2$ (4×400 mL). The combined organic layers were dried with $MgSO_4$ and concentrated to give 37 g of the piperazine free base. The free base was recrystallized three times from hexane (890, 600 and 450 mL) to give 16 g of piperazine (>99.9% ee of enantiomer A). $[\alpha]_D^{24.7°}$ $^C$=–45.0°(MeOH)

Step 4: The precipitated salts from step 1 were combined and heated in methanol (220 mL) until all of the material dissolved. EtOAc (2.2 L) was added to this solution and allowed to stand at ambient temperature overnight. The solvent phase was decanted from the precipitated salt and dried in vacuo to give ~43 g of piperazine salt (93% ee of enantiomer B).

Step 5: A 12.3 g portion of salt (75% ee of enantiomer B) prepared by an analogous procedure to that in step 4 was dissolved in 0.5M NaOH (400 mL) and extracted with $CH_2Cl_2$ (4×155 mL). The combined organic layers were dried with $MgSO_4$ and concentrated to give 3.72 g of the piperazine free base. The free base was recrystallized twice from hexane (90 and 70 mL) to give 2.1 g of piperazine (98% ee of enantiomer B).

C. Analytical procedure for measuring piperazine enantiomeric purity.

The enantiomeric purity of the piperazine was measured by chiral HPLC analysis of the di-tert-butoxycarbonyl piperazine derivative. The di-tert-butoxycarbonyl derivative was prepared by adding a small piperazine sample (free base or salt)(~0.2 mg) to di-tert-butyl dicarbonate (~1 mg) and methanol (0.5 mL) and heating at 80° C. for 1 h. If the piperazine sample is a salt, triethylamine (20 µL) is also added. The derivative was analyzed by HPLC using a ChiralPak AD column eluting with 95:5 hexane-isopropyl alcohol.

PREPARATIVE EXAMPLE 2

(+,−)-[3,5-dimethylbenzoyl]-3-(3,4-dichlorophenyl) piperazine

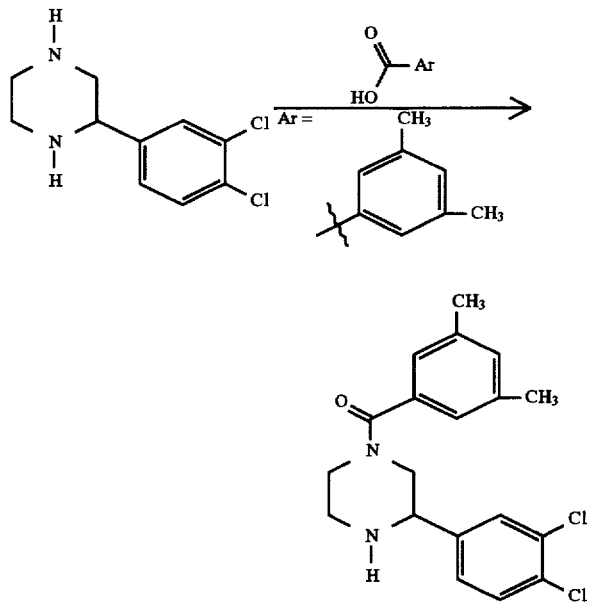

To a cooled solution of CH₂Cl₂ (600 mL) containing 2-(3,4-dichlorophenyl)piperazine (6.934 g, 30 mmol), 3,5-dimethylbenzoic acid (4.55 g, 30 mmol), and N-hydroxybenzotriazole monohydrate (4.05 g, 30 mmol) at −20° C. were added Et₃N (4.2 mL, 30 mmol) and N,N-dimethylaminopropylethylcarbodimide (DEC) (5.86 g, 30 mmol) under nitrogen. The reaction was kept at −20° C. for an hour and gradually warmed to RT overnight. After stirring 22 hours, the reaction was complete and CH₂Cl₂ (200 mL) was added. The organic solution was washed with brine (150 mL, 3×), dried over MgSO₄, filtered and concentrated under vacuum to give 8.2 g of crude product. The product was crystallized from CH₂Cl₂/Hexane to give a light yellow solid (6.3 g, 17.34 mmol, 57.8%). M.p. 139°–141° C.; FAB MS [M+1]⁺ ³⁵Cl 363.1.

PREPARATIVE EXAMPLE 3

(+,−)-bromoacetyl-2-(3,4-dichlorophenyl)-4-(3,5-dimethylbenzoyl)piperazine

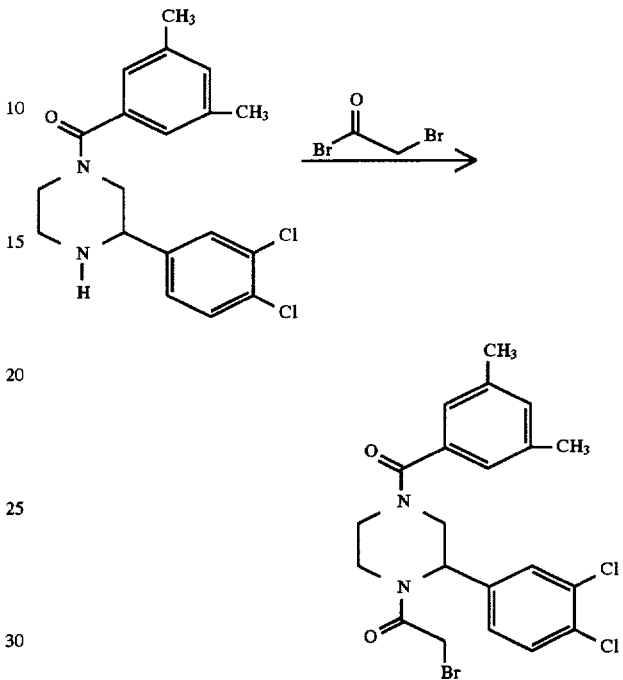

To a cooled solution of (+,−)-[3,5-dimethylbenzoyl]-3-(3,4-dichlorophenyl)piperazine (11.5 g, 31.65 mmol) in CH₂Cl₂ (200 mL) at 0° C. was added Hünig's base (4.5 g, 35 mmol) and bromoacetyl bromide (6.4 g, 31.65 mmol). The solution was stirred at 0° C. overnight under N₂. After completion the reaction was diluted with CH₂Cl₂ (400 mL) and washed with brine (300 mL, 2×), dried over MgSO₄, filtered and concentrated. The crude material was purified by flash grade silica gel chromatography, eluting with 2% [NH₄OH/MeOH (1:9)]/98% CH₂Cl₂ to give the title compound as a light yellow solid (7.1 g, 47.3%), m.p. 77°–79° C., FAB MS [M+1]⁺ ³⁵Cl, ⁷⁹Br 482.9, 484.9.

PREPARATIVE EXAMPLE 4

(+)-[3,5-dimethylbenzoyl]-3-(3,4-dichlorophenyl) piperazine (Enantiomer B)

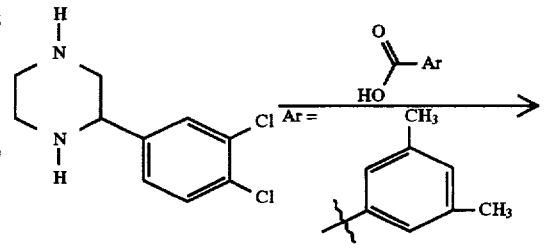

51

-continued

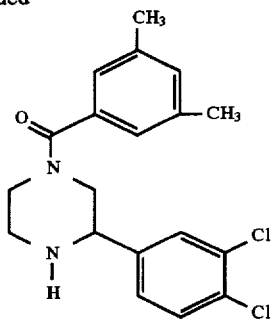

The title compound was prepared by an analogous method to that described in Example 2 using (−)-2-(3,4-dichlorophenyl)piperazine in place of (+,−)-2-(3,4-dichlorophenyl)piperazine. m.p. 97°–100° C.; FAB MS [M+1]$^+$ $^{35}$Cl 363. 1; [α]$_D^{22.5°}$ $^C$=+87.2°(MeOH).

EXAMPLE 1

2-(3,4-Dichlorophenyl)-4-(3,5-dimethylbenzoyl)-1-[3-[1,2-dihydro-1-(methanesulfonyl)spiro[3H-indole-3,4'-piperidine]-1'-yl]-1-oxopropyl]-piperazine (Enantiomer B)

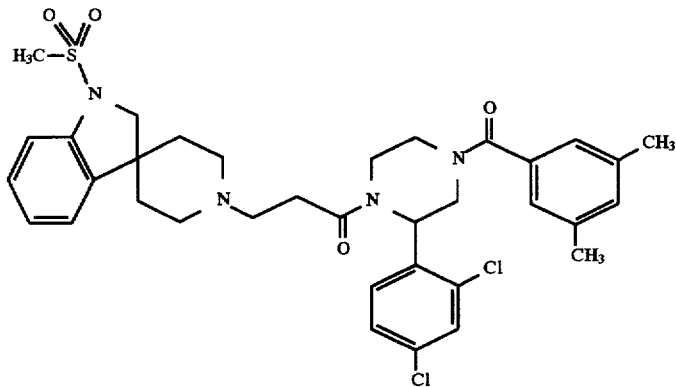

A cooled CH$_2$Cl$_2$ (3 mL) solution of the product of Preparative Example 4 (146 mg, 0.40 mmol) and Hünig's base (0.11 mL, 0.80 mmol) at −78° C. was treated with 3-chloropropionyl chloride (0.038 mL, 0.40 mmol) and warmed to room temperature for 1 h. 1-Methanesulfonyl-spiro(indoline-3,4'-piperidine) (82 mg, 0.30 mmol) (prepared according to the procedure in Ong et al, *J. Med. Chem.*, 26, (1983), p. 981–986) was added to the reaction mixture and the resultant mixture was stirred for 48 h at room temperature. The reaction mixture was concentrated and purified by silica gel chromatography, eluting with 25:1:0.1 CH$_2$Cl$_2$:CH$_3$OH:conc. aq. NH$_3$ to give 39 mg of the title compound as a white solid. HRMS (FAB, M+H$^+$): m/e calc'd [C$_{35}$H$_{41}$Cl$_2$N$_4$O$_4$S]$^+$: 683.2226, found 683.2214.

EXAMPLE 2

2-(3,4-Dichlorophenyl)-1-[3-[3,4-dihydro-4-oxo-6-methoxy-spiro[2H-1-benzopyran-2,4'-piperidin]-1'-yl]-1-oxopropyl]-4-(3,5-dimethylbenzoyl)piperazine (Enantiomer B)

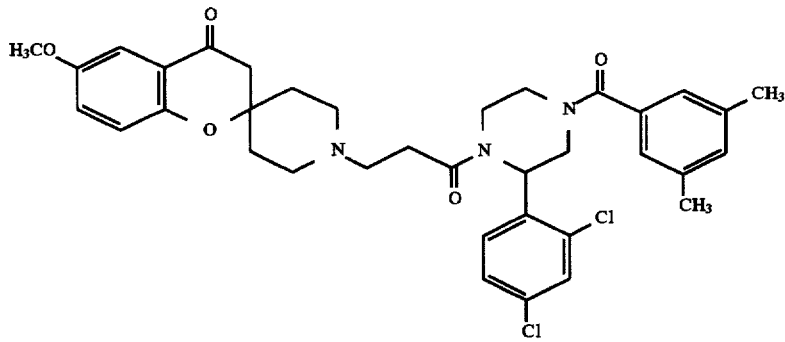

Using a method similar to that described in Example 1, substituting 6-methoxy-spiro[2H-1-benzopyran-2,4'- piperidine] (prepared according to the procedure described in Yamato et al, *Chem. Pharm. Bull.*, 29 (1981), p. 3494–3498) for the spiro compound, the title compound was prepared. HRMS (FAB, M+H⁺): m/e calc'd [C₃₆H₄₀Cl₂N₃O₅]⁺: 664.2345, found 664.2365.

EXAMPLE 3

2-(3,4-Dichlorophenyl)-4-(3,5-dimethylbenzoyl)-1-[3-(1-phenyl-4-oxo-1,3,8-triazaspiro[4.5]decan-8-yl)-1-oxopropyl]piperazine (Enantiomer B)

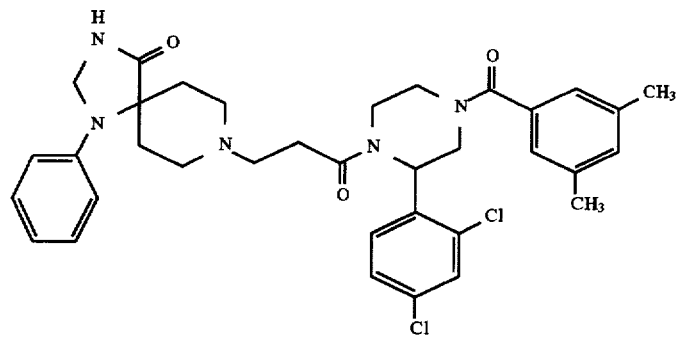

Using a method similar to that described in Example 1, substituting 1-phenyl-1,3,8-triazaspiro[4.5]decan-4-one for the spiro compound, the title compound was prepared. HRMS (FAB, M+H⁺): m/e calc'd [C₃₅H₄₀Cl₂N₅O₃]⁺: 648.2508, found 648.2509.

What is claimed is:

1. A compound of the formula:

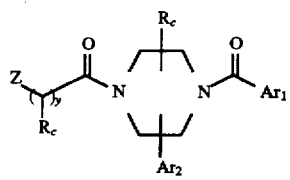

wherein y is 1 to 3;

each $R_c$ is independently selected from the group consisting of H, $C_1$–$C_6$ alkyl and —(CH₂)$_{n1}$-R₄, wherein n₁ is 1 to 6, with the proviso that no more than one $R_c$ is other than H in the

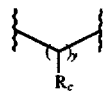

moiety;

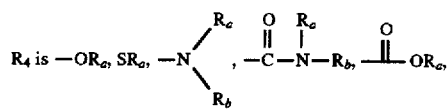

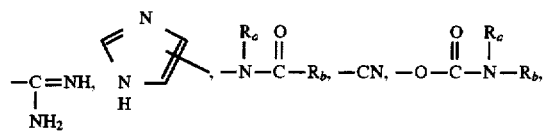

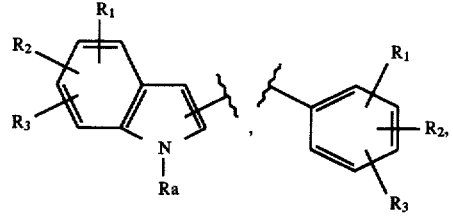

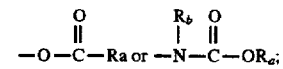

each $R_a$ and $R_b$ is independently selected from the group consisting of H, $C_1$–$C_6$ alkyl, phenyl, substituted phenyl, benzyl, substituted benzyl and allyl; with the proviso that when R₄ is

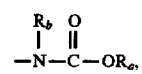

$R_a$ is not H; or when $R_a$ and $R_b$ are attached to the same nitrogen, then $R_a$ and $R_b$, together with the nitrogen to which they are attached, can form a 4 to 7 member ring;

each R₁ and R₂ is independently selected from the group consisting of H, $C_1$–$C_6$ alkyl, —CF₃, —C₂F₅, Cl, Br, I, F, —NO₂, —OR$_a$, —CN, —NR$_a$R$_b$,

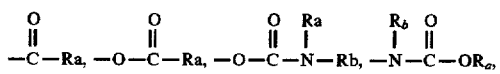

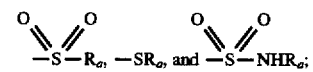

provided $R_a$ is not H in
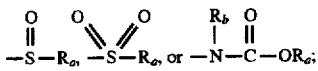
or when $R_1$ and $R_2$ are on adjacent carbons on a ring, they can form
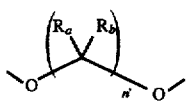
wherein n' is 1 or 2;
each $R_3$ is independently selected from the group consisting of H, $C_1$-$C_6$ alkyl, —$CF_3$, —$C_2F_5$,
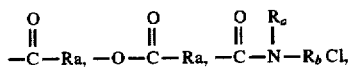
Br, I, F, —$OR_a$, —$OCF_3$ or phenyl;
$Ar_1$ is
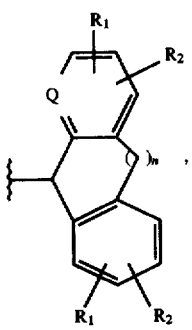
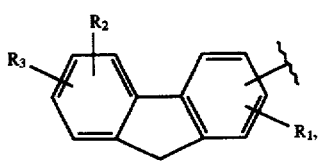
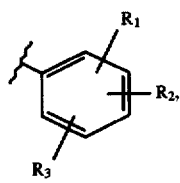
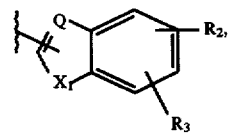
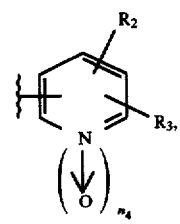
-continued
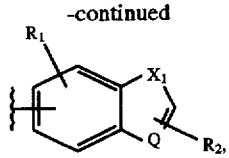
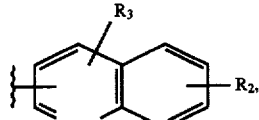
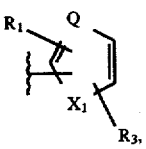
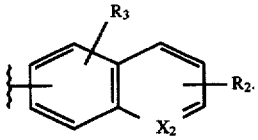
each $X_1$ is independently —O—, —S— or —$NR_a$—;
each $X_2$ is independently =CH— or —N=;
$n_4$ is 0 or 1;
Q is =N— or =CH—;
$Ar_2$ is
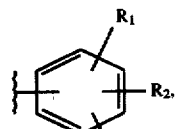
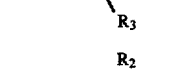
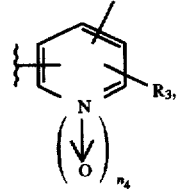
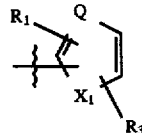
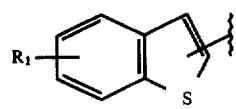
or
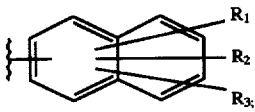

-continued

Z is

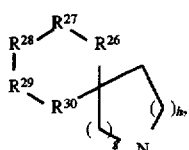

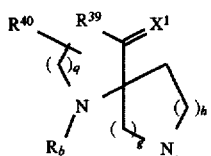

or

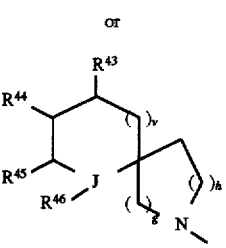

wherein the nitrogen in the unsubstituted ring is optionally quaternized with $C_{1-4}$ alkyl or phenyl-$C_{1-4}$ alkyl or is optionally present as the Noxide ($N^+O^-$); g and h are each independently 0, 1, 2, 3, 4, or 5, with the proviso that g+h is equal to 1, 2, 3, 4, or 5;

v is 0, 1 or 2;

$R^{26}$ is selected from the group consisting of
(1) a covalent bond
(2) $C_{1-3}$ alkylene, unsubstituted or substituted with a substituent selected from the group consisting of =O, —OH, —$OR^{35}$, halogeno, —$CF_3$, phenyl or mono, di or trisubstituted phenyl, wherein the substituents on the phenyl are independently selected from —OH, —CN, halogeno and —$CF_3$,
(3) $S(O)_k$
(4) ($C_{1-3}$ alkylene)-$S(O)_k$
(5) $S(O)_k$—($C_{1-2}$ alkylene)
(6) $S(O)_k$NH
(7) $S(O)_j$—$NR^{35}$
(8) $S(O)_j$—$NR^{35}$—($C_{1-2}$ alkylene)
(9) CONH
(10) $CONR^{35}$—($C_{1-2}$ alkylene)
(11) $CO_2$ and
(12) $CO_2$—($C_{1-2}$ alkylene)
wherein j is 1 or 2 and k is 0, 1 or 2;

$R^{27}$ is —$NR^{37}$—, —O—, —S—, —S(O)—, or —$SO_2$—, with the proviso that when $R^{26}$ is a covalent bond and $R^{28}$ is $C_{1-3}$ alkyl, $R^{27}$ must be $NR^{37}$;

$R^{37}$ is selected from a group consisting of:
(1) H,
(2) $C_{1-8}$ linear or branched alkyl, unsubstituted, mono-substituted or multiply substituted with —$OR^{35}$, =O, —$NHCOR^{35}$, —$NR^{35}R^{36}$, —CN, -halogeno, —$CF_3$, -phenyl or substituted phenyl, wherein the substituents on phenyl are selected from the group consisting of —OH, —CN, halogeno and —$CF_3$;
(3) $S(O)R^{38}$, wherein $R^{38}$ is $C_{1-6}$ linear or branched alkyl, unsubstituted, mono di or trisubstituted with a substituent selected from the group consisting of =O, —CN, —$OR^{35}$, —$NR^{35}R^{36}$, —$NR^{36}OR^{36}$,-halogeno,—$CF_3$, -phenyl or mono, di or trisubstituted phenyl, wherein the substituents on the phenyl are independently selected from the group consisting of —OH, =O, —CN, —$NR^{35}R^{36}$, —$NR^{35}COR^{36}$, -halogeno, —$CF_3$ and $C_{1-3}$ alkyl;
(4) $SO_2R^{38}$,
(5) $COR^{38}$,
(6) $CO_2R^{38}$;
(7) $CONR^{36}R^{38}$;

$R^{28}$ is selected from the group consisting of
(1) a covalent bond
(2) $C_{1-3}$ alkylene, unsubstituted or substituted with a substituent selected from the group consisting of =O, —$OR^{35}$, halogeno, —$CF_3$, phenyl or mono, di or trisubstituted phenyl, wherein the substituents on the phenyl are independently selected from the group consisting of —$OR^{35}$, halogeno and —$CF_3$;
(3) $S(O)_k$
(4) ($C_{1-3}$ alkylene)-$S(O)_k$
(5) $S(O)_k$—($C_{1-2}$ alkylene)
(6) $NHS(O)_j$
(7) $NH(C_{1-2}$ alkylene)-$S(O)_j$
(8) $S(O)_jNR^{35}$
(9) $S(O)_j$—$NR^{35}$—($C_{1-2}$ alkylene)
(10) NHCO—($C_{1-2}$ alkylene)
(11) $NR^{35}CO$
(12) $NR^{35}$—($C_{1-2}$ alkylene)-CO
(13) O(CO) and
(14) ($C_{1-2}$ alkyl)O(CO);

$R^{29}$-$R^{30}$ considered together are 2 adjoining atoms of the ring

said ring being a phenyl, naphthyl or heteroaryl group, and wherein the phenyl, naphthyl or heteroaryl group is unsubstituted, mono, di or tri substituted, wherein heteroaryl is selected from the group consisting of benzimidazolyl, benzofuranyl, benzoxazolyl, furanyl, imidazolyl, indolyl, isoxazolyl, isothiazolyl, oxadiazolyl, oxazolyl, pyrazinyl, pyrazolyl, pyridyl, pyrimidyl, pyrrolyl, quinolyl, tetrazolyl, thiadiazolyl, thiazolyl, thienyl and triazolyl; and wherein the substituents are independently selected from the group consisting of:
(a) $C_{1-6}$ alkyl, branched or unbranched, unsubstituted or mono or disubstituted by hydroxy
(b) =O
(c) $OR^{35}$
(d) halogeno
(e) $CF_3$
(f) $NO_2$
(g) CN
(h) $NR^{35}R^{36}$
(i) $NR^{35}COR^{36}$
(j) $NR^{35}CO_2R^{36}$
(k) $NR^{35}S(O)_jR^{36}$
(l) $CONR^{35}R^{36}$
(m) $COR^{35}$
(n) $CO_2R^{35}$
(o) $S(O)_jR^{35}$
(p) heteroaryl, or mono or di substituted heteroaryl, wherein heteroaryl is as defined above and the substituents are selected from the group consisting of: $C_{1-6}$ alkyl, branched or unbranched, unsubstituted or mono or disubstituted by OH; =O; $OR^{35}$; $CF_3$; —$NO_2$; CN; $NR^{35}R^{36}$; $NR^{35}COR^{36}$; $NR^{35}CO_2R^{36}$; $NR^{35}S(O)_iR^{36}$; $CONR^{35}R^{36}$; $COR^{35}$; $CO_2R^{35}$; $S(O)_iR^{35}$; and phenyl;

$R^{35}$ and $R^{36}$ are independently selected from:
 (a) H,
 (b) $C_{1-6}$ alkyl, or mono or disubstituted $C_{1-6}$ alkyl, wherein the substituents independently selected from the group consisting of phenyl, unsubstituted or substituted with —OH, $C_{1-3}$ alkyl, —CN, halogeno, —$CF_3$ or $C_{1-4}$ alkoxy; —OH; =O; —CN; halogeno; or —$CF_3$;
 (c) phenyl, pyridinyl or thiophene, or mono, di or trisubstituted phenyl, pyridinyl or thiophene, wherein the substituents are independently selected from the group consisting of —OH, $C_{1-4}$ alkyl, —CN, halogeno and —$CF_3$;
 (d) $C_{1-3}$ alkyloxy, or $R^{35}$ and $R^{36}$ are joined together to form a 5-, 6-, or 7-membered monocyclic saturated ring containing 1 or 2 heteroatoms independently selected from nitrogen, oxygen, and sulfur, and in which the ring is unsubstituted or mono or disubstituted, wherein the substituents are independently selected from the group consisting of —OH, =O, —CN, halogeno and —$CF_3$;

q is 1 or 2;

$X^1$ is =O or =S;

$R^{39}$ is —$NR_b$— or —$CH_2$—;

$R^{40}$ is H, $C_1$-$C_6$ alkyl, =O, phenyl, substituted phenyl, benzyl, substituted benzyl or allyl J is carbon and $R^{43}$, $R^{44}$, $R^{45}$ and $R^{46}$ are independently selected from the group consisting of H, —OH, =O, —$NR^{47}R^{48}$ or —$NR^{47}C(O)$—$NR^{47}R^{48}$, wherein the nitrogen of —$NR^{47}R^{48}$ is optionally quaternized with $C_{1-4}$ alkyl or phenyl-$C_{1-4}$ alkyl or is optionally present as the N-oxide; or $R^{43}$ and $R^{44}$, or $R^{44}$ and $R^{45}$, together form a carbon-carbon bond; or $R^{43}$ and $R^{44}$ or $R^{44}$ and $R^{45}$, or $R^{45}$ and $R^{46}$, together with the carbons to which they are attached form an aryl or heteroaryl ring, wherein heteroaryl is as defined above, and wherein the aryl or heteroaryl group is unsubstituted, mono, di or tri substituted, wherein the substituents are independently selected from the group consisting of:
 (a) $C_{1-6}$ alkyl, branched or unbranched, unsubstituted or mono or disubstituted by hydroxy
 (b) =O
 (c) $OR^{47}$
 (d) halogeno
 (e) $CF_3$
 (f) $NO_2$
 (g) CN
 (h) $NR^{47}R^{48}$
 (i) $NR^{47}COR^{48}$
 (j) $NR^{47}CO_2R^{48}$
 (k) $NR^{47}S(O)_iR^{48}$
 (l) $CONR^{47}R^{48}$
 (m) $COR^{47}$
 (n) $CO_2R^{47}$
 (o) $S(O)_iR^{47}$
 (p) heteroaryl, or mono or di substituted heteroaryl, wherein heteroaryl is as defined above and the substituents are selected from the group consisting of: $C_{1-6}$ alkyl, branched or unbranched, unsubstituted or mono or disubstituted by OH; =O; $OR^{47}$; $CF_3$; —$NO_2$; CN; $NR^{47}R^{48}$;

$NR^{47}COR^{48}$; $NR^{47}CO_2R^{48}$; $NR^{47}S(O)_iR^{48}$; $CONR^{47}R^{48}$; $COR^{47}$; $CO_2R^{47}$;

$S(O)_iR^{47}$; and phenyl;

or $R^{43}$, $R^{44}$ and $R^{45}$ are as defined above and J-$R^{46}$ is oxygen or $S(O)_i$, wherein i is 0, 1, or 2; and $R^{47}$, $R^{47'}$ and $R^{48}$ are independently selected from the group consisting of:
 (a) H,
 (b) $C_{1-6}$ alkyl, or mono or disubstituted $C_{1-6}$ alkyl, wherein the substituents independently selected from the group consisting of phenyl, —OH, =O, —CN, halogeno and —$CF_3$;
 (c) phenyl, naphthyl, or mono, di or trisubstituted phenyl or naphthyl, wherein the substituents are independently selected from the group consisting of —OH, $C_{1-3}$ alkyl, —CN, halogeno and —$CF_3$; and
 (d) $C_{1-3}$ alkyloxy; or $R^{47}$ and $R^{48}$ are joined together to form a 5-, 6-, or 7-membered monocyclic saturated ring containing 1 or 2 heteroatoms independently selected from nitrogen, oxygen, and sulfur, and in which the ring is unsubstituted or mono or disubstituted, wherein the substituents are independently selected from the group consisting of —OH, =O, —CN, halogeno and —$CF_3$;

or an enantiomer or diastereomer thereof, or a pharmaceutically acceptable salt thereof.

2. A compound according to claim 1 wherein Z is

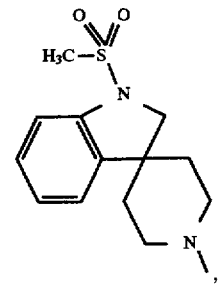

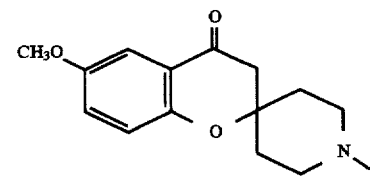

or

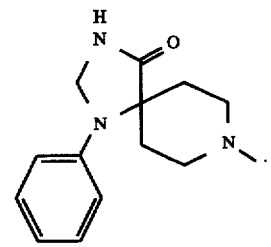

3. A composition comprising a neurokinin antagonistic effective amount of a compound according to claim 1 and a pharmaceutically acceptable carrier material.

4. A method for inducing neurokinin antagonism which comprises administering a neurokinin antagonistic effective amount of a compound according to claim 1 to a mammal in need thereof.

5. A method for treating chronic airway diseases selected from the group consisting of asthma and allergies; inflammatory diseases selected from the group consisting of inflammatory bowel disease, psoriasis, fibrositos, osteoarthritis, and rheumatoid arthritis; migraine; central nervous system disorders selected from the group consisting of depression, emesis, psychosis, dementia, and Alzheimer's disease; Down's syndrome; neuropathy; multiple sclerosis; ophthalmic disorders; conjunctivitis; auto immune disorders; graft rejection; systemic lupus erythematosus; GI disorders selected from the group consisting of Crohn's disease and ulcerative colitis; disorders of bladder function; circulatory disorders selected from the group consisting of angina; Raynaud's disease; coughing and pain, which comprises administering a therapeutically effective amount of a compound according to claim 1.

6. A compound according to claim 1 selected from the group consisting of:
2-(3,4-dichlorophenyl)-4-(3,5-dimethylbenzoyl)-1-[3-[1,2-dihydro-1-(methanesulfonyl)spiro[3H-indole-3,4'-piperidine]-1'-yl]-1-oxopropyl]piperazine;
2-(3,4-dichlorophenyl)-1-[3-[3,4-dihydro-4-oxo-6-methoxy-spiro[2H-1-benzopyran-2,4'-piperidin]-1'-yl]-1-oxopropyl]-4-(3,5-dimethyl-benzoyl)piperazine; and
2-(3,4-dichlorophenyl)-4-(3,5-dimethylbenzoyl)-1-[3-(1-phenyl-4-oxo-1,3,8-triazaspiro[4.5]decan-8-yl)-1-oxopropyl]piperazine.

* * * * *